United States Patent
Yamanishi et al.

(10) Patent No.: US 9,949,465 B2
(45) Date of Patent: Apr. 24, 2018

(54) ATOPIC DERMATITIS MODEL ANIMAL AND USE THEREOF

(71) Applicants: HYOGO COLLEGE OF MEDICINE, Nishinomiya-shi, Hyogo (JP); MIE UNIVERSITY, Tsu-shi, Mie (JP)

(72) Inventors: Kiyofumi Yamanishi, Nishinomiya (JP); Hitoshi Mizutani, Tsu (JP); Yasutomo Imai, Nishinomiya (JP); Tomohiro Yoshimoto, Nishinomiya (JP); Kenji Nakanishi, Nishinomiya (JP)

(73) Assignees: Hyogo College of Medicine, Nishinomiya (JP); Mie University, Tsu (JP)

( * ) Notice: Subject to any disclaimer, the term of this patent is extended or adjusted under 35 U.S.C. 154(b) by 0 days.

(21) Appl. No.: 14/888,398

(22) PCT Filed: Apr. 30, 2014

(86) PCT No.: PCT/JP2014/061931
§ 371 (c)(1),
(2) Date: Oct. 30, 2015

(87) PCT Pub. No.: WO2014/178392
PCT Pub. Date: Nov. 6, 2014

(65) Prior Publication Data
US 2016/0057978 A1    Mar. 3, 2016

(30) Foreign Application Priority Data

May 1, 2013   (JP) .................................. 2013-096637

(51) Int. Cl.
*A01K 67/027*    (2006.01)
*C07K 14/54*     (2006.01)
*A61K 49/00*     (2006.01)

(52) U.S. Cl.
CPC ...... *A01K 67/0278* (2013.01); *A01K 67/0275* (2013.01); *A61K 49/0008* (2013.01); *C07K 14/54* (2013.01); *A01K 2217/052* (2013.01); *A01K 2217/206* (2013.01); *A01K 2227/105* (2013.01); *A01K 2267/035* (2013.01); *A01K 2267/0368* (2013.01)

(58) Field of Classification Search
CPC .................................................. A01K 67/0278
See application file for complete search history.

(56) References Cited

U.S. PATENT DOCUMENTS

2003/0159163 A1    8/2003   Mizutani

FOREIGN PATENT DOCUMENTS

EP          1405560 A1    4/2004
WO   WO 2001/095710 A1   12/2001

OTHER PUBLICATIONS

Munoz et al. (2009) Stem Cell Rev. and Rep., vol. 5, 6-9, pp. 6 and 9).*
Tang et al (Anim Reprod, 12(1): 93-104, 2015).*
Yamanaka, et al (The Journal of Immunology, 2000, 165: 997-1003).*
Keefer (Animal Reproduction Science 82-83: 5-12, 2004).*
Ristevski, Molecular Biotechnology, 2005, 153-163.*
Gama Sosa et al Brain Struct Funct (2010) 214:91-109.*
Smith, et al Journal of Biotechnology 99 (2002) 1-22.*
Sigmund Arteroscler Throm Vasc Biol 20:1426.*
Meephansan et al., "Regulation of IL-33 expression by IFN-γ and Tumor Necrosis Factor-α in Normal Human Epidermal Keratinocytes," *Journal of Investigative Dermatology*; 132(11): 2593-2600 (2012).
European Patent Office, Supplementary European Search Report in European Patent Application No. 14791230 (dated Nov. 2, 2016).
Gutermuth et al., *Int. Arch. Allergy Immunol.*, 135: 262-276 (2004).
Hueber et al., *Eur. J. Immunol.*, 41: 2229-2237 (2011).
Imai et al., *PNAS*, 110: 13921-13926 (20013).
Keller et al., *Biochemical and Biophysical Research Communications*, 417: 217-222 (2012).
Neill et al., *Nature*, 464: 1367-1370 (2010).
Rankin et al., *The Journal of Immunology*, 184: 1526-1535 (2010).
Savinko et al., *J. Invest. Dermatol.*, 132: 1392-1400 (2012).
Shiina et al., *The Journal of Biological Chemistry*, 279(53): 55493-55498 (2004).
Xiang et al., *Immunology Letters*, 131: 159-165 (2010).
Japanese Patent Office, International Search Report in International Patent Application No. PCT/JP2014/061931 (dated Jul. 22, 2014).
Pushparaj et al., "The cytokine interleukin-33 mediates anaphylactic shock," *Proc. Natl. Acad. Sci. U.S.A.*, 106(24): 9773-9778 (2009) and subsequent retraction published at 109(34): 13877 (2012).

* cited by examiner

*Primary Examiner* — Anoop K Singh
*Assistant Examiner* — Magdalene K Sgagias
(74) *Attorney, Agent, or Firm* — Leydig, Voit & Mayer, Ltd.

(57) ABSTRACT

The present invention provides a transgenic non-human mammal retaining, in a specifically expressible state, a DNA encoding IL-33 in the skin, and having one or more features selected from the group consisting of
(1) spontaneous onset of dermatitis,
(2) increase in the number of inflammatory cells,
(3) increase in total IgE concentration, histamine concentration, cytokine concentration and/or chemokine concentration, and
(4) increase in scratching time,
under SPF (specific pathogen free) breeding conditions, as compared to a corresponding non-transgenic non-human mammal, and the like.

6 Claims, 16 Drawing Sheets

ATOPIC DERMATITIS MODEL ANIMAL AND USE THEREOF

CROSS-REFERENCE TO RELATED APPLICATIONS

This patent application is the U.S. national phase of International Patent Application No. PCT/JP2014/061931, filed Apr. 30, 2014, which claims the benefit of Japanese Patent Application No. 2013-096637, filed on May 1, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,426 bytes ASCII (Text) file named "722280SequenceListing.txt," created Oct. 30, 2015.

TECHNICAL FIELD

The present invention relates to a transgenic non-human mammal that retains IL-33 gene in a specifically expressible state in the skin, a screening method or an evaluation method of a prophylactic or therapeutic drug for atopic dermatitis using same and the like.

BACKGROUND ART

Atopic dermatitis is a pruritic, chronically recurrent inflammatory dermatosis, which has a genetic background and characteristically accompanies high IgE level in the serum. In addition, mast cells and eosinophils gather in the lesion, and eosinophils in the blood also increase. While the mechanism of the onset of atopic dermatitis has not been completely elucidated, activation of basophils and mast cells induced by crosslinking of immunoglobulin (hereinafter to be indicated as Ig) E molecules bound to FcεR on activated T cells, basophils or mast cells, which results in the production of Th2-related cytokine and chemical mediator, is considered to be important. The above-mentioned cytokine refers to interleukin (hereinafter to be indicated as IL)-4, IL-13 and IL-5, and the chemical mediator refers to histamine, serotonin and the like. In this case, antigen specific IgE plays an important role particularly in the activation of basophils and mast cells; however, this does not apply to innate atopic dermatitis for which antigen specificity is not clear and the detail is unknown, though involvement of external stimulation and infection, IL-18 and the like is suggested.

As genetically-engineered atopic dermatitis model mice, 7 lineages [IL-4 Tg, CASP1 Tg, IL-18 Tg, IL-31 Tg, Re1B-KO, CatE-KO (non-patent document 1), MAIL-KO (non-patent document 2)] have been reported.

However, atopic dermatitis model mouse generated by genetic engineering does not necessarily reflect the actual features of atopic dermatitis. For example, some of the models reported as atopic dermatitis models generated by genetic engineering are models (CASP1 Tg, IL-18 Tg, IL-4 Tg) showing enhanced expression of genes; however, they show localization of high expression of genes generally absent in the skin of atopic dermatitis patients, or eosinophil and neutrophil are not found in dermatitis tissues and numerical values of IgE do not show variation (IL-31 Tg), and the like. Therefore, it is considered that they are not necessarily disease models appropriately reflecting atopic dermatitis in human. In addition, Re1B-KO mouse showing no pruritus symptoms and MAIL(IkBζ)-KO mouse showing very high perinatal mortality rate and severe dermatitis symptoms and the like are imperfect as atopic dermatitis models. As such, when these model mice are used for the evaluation of atopic dermatitis, they are feared to reflect non-actual conditions.

In recent years, study of atopic dermatitis has progressed and new findings have been reported. Recently, an increase in the expression of IL-33 in the nucleus of epidermal keratinocytes of the skin of atopic dermatitis patients has been reported (non-patent document 3). IL-33 has been identified as a cytokine belonging to the IL-1 family having an amino acid sequence with high homology with IL-1βand IL-18, and ST2 is the receptor thereof. Since ST2 is expressed on Th2 cells and cells involved in allergy (basophils, mast cells, eosinophils, type 2 innate lymphoid cells), IL-33 suggested to be involved in Th2 type allergic diseases. However, a report indicates that when mouse recombinant IL-33 is directly administered topically into the skin dermis, a scleroderma-like reaction accompanying an increase in the collagenous fibers of dermis occurs, and changes of epidermis do not accompany (non-patent document 4); another report indicates that psoriasis-like dermatitis accompanying epidermis thickening occurs (non-patent document 5). Therefore, an influence of IL-33 on the skin has not been clear. In such situation, a transgenic animal highly expressing IL-33 in the skin has not been found to date, and the phenotype thereof is also unknown.

DOCUMENT LIST

Non-Patent Documents non-patent document 1: Gutermuth J et al. Int Arch Allergy Immunol, 2004, 135, 262-276
non-patent document 2: Shiina T et al. J Biol Chem. 2004, 279, 55493-55498
non-patent document 3: Savinko T et al. J Invest Dermatol, 2012, 132: 1392-1400
non-patent document 4: Rankin A L et al. J Immunol, 2010, 184:1526-1535
non-patent document 5: Hueber A J et al. Eur J Immunol, 2011, 41:2229-2237

SUMMARY OF THE INVENTION

Problems to be Solved by the Invention

An object of the present invention is to produce and analyze an IL-33 transgenic non-human mammal that shows skin specific overexpression, in an attempt to elucidate the in vivo function of IL-33 gene, and further, to provide a screening method for a prophylactic or therapeutic drug for atopic dermatitis or an evaluation method of a prophylactic or therapeutic drug for atopic dermatitis, by using the obtained transgenic non-human mammal.

Means of Solving the Problems

The present inventors generated transgenic (Tg) mice by introducing mouse IL-33 gene under the control of a keratin promoter. As a result, under SPF (specific pathogen free) (free of infection with a particular pathogenic microorganism) breeding conditions, the Tg mice showed spontaneous onset of dermatitis, an increase in the number of inflammatory cells, an increase in the total IgE concentration, histamine concentration, cytokine concentration and chemokine concentration, and an increase in scratching behavior time, as compared to the corresponding non-transgenic mice. In other words, the features of the transgenic mouse in the present m invention are the same as the observations found in atopic dermatitis patients. Furthermore, known anti-histamine drugs and steroid drugs succeeded in decreasing the scratching time.

The present inventors conducted further investigations based on these findings, and completed the present invention.

That is, the present invention provides

[1] A transgenic non-human mammal retaining a DNA encoding IL-33 in a specifically expressible state in the skin, and having one or more features selected from the group consisting of
(1) spontaneous onset of dermatitis,
(2) increase in the number of inflammatory cells,
(3) increase in total IgE concentration, histamine concentration, cytokine concentration and/or chemokine concentration, and
(4) increase in scratching time, under SPF (specific pathogen free) breeding conditions, as compared to a corresponding non-transgenic non-human mammal;
[2] the non-human mammal of [1], wherein the DNA encoding IL-33 is under regulation of keratin promoter;
[3] the non-human mammal of [2], wherein the keratin promoter is a human keratin 14 promoter;
[4] the non-human mammal of any one of [1]-[3], wherein IL-33 has the same or substantially the same amino acid sequence as the amino acid sequence shown by SEQ ID NO:2;
[5] the non-human mammal of any one of [1]-[4], wherein the inflammatory cells are cells selected from the group consisting of eosinophils, mast cells and type 2 innate lymphoid cells;
[6] the non-human mammal of any one of [1]-[5], wherein the cytokine is IL-4, IL-5 or IL-13;
[7] the non-human mammal of any one of [1]-[6], wherein the chemokine is CCL2, CCL4, CCL5 or CCL11;
[8] the non-human mammal of any one of [1]-[7], wherein the scratching time or symptoms of dermatitis decreases due to an anti-histamine drug or a steroid drug;
[9] the non-human mammal of any one of [1]-[8], wherein the non-human mammal is a mouse;
[10] a method of screening for a therapeutic agent for atopic dermatitis, comprising, under SPF (specific pathogen free) breeding conditions, applying a test compound to the non-human mammal of any one of [1]-[9], and measuring one or more items selected from the group consisting of (1) rash score, (2) number of inflammatory cells, (3) total IgE concentration, histamine concentration, cytokine concentration and/or chemokine concentration, and (4) scratching time, and selecting a test substance that improves the aforementioned measured item as compared to non-administration of the test compound;
[11] a method of evaluating an effect of a prophylactic or therapeutic drug for atopic dermatitis, comprising, under SPF (specific pathogen free) breeding conditions, applying a prophylactic or therapeutic drug for atopic dermatitis to the non-human mammal of any one of [1]-[9], and measuring one or more items selected from the group consisting of (1) rash score, (2) number of inflammatory cells, (3) total IgE concentration, histamine concentration, cytokine concentration and/or chemokine concentration, and (4) scratching time, and comparing the aforementioned measured item with non-administration of the prophylactic or therapeutic drug for atopic dermatitis.

Effect of the Invention

The IL-33 transgenic non-human mammal of the present invention shows a phenotype more reflecting the symptoms of atopic dermatitis in human, is useful as an evaluation system of the role of IL-33 in atopic dermatitis in the living body, and further, can be used for screening for or efficacy evaluation of a prophylactic or therapeutic drug for atopic dermatitis.

DESCRIPTION OF EMBODIMENTS

Figure 1:
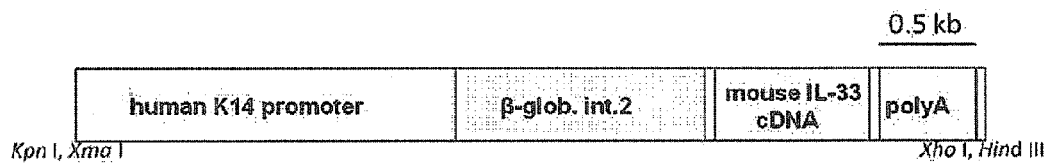
FIG. 1 shows the structure of 4.0 kb linear DNA containing human keratin14 promoter, rabbit β globin intron 2, mouse IL-33 variant 1 cDNA, and human keratin 14 poly A signal.

A transgenic non-human mammal retaining a DNA that encodes IL-33 in a specifically expressible state in the skin (hereinafter sometimes referred to as "the Tg animal of the present invention") stably retains a DNA that encodes IL-33 in a specifically expressible state in the skin. "Stably retains" means that the DNA that encodes IL-33 is permanently present, in a specifically expressible state in the skin, in the cells of the animal. While the DNA may be integrated into a host chromosome, or may be stably present as an extra-chromosomal DNA, the DNA is preferably retained in an integrated state into a host chromosome.

The Tg animal of the present invention is prepared by introducing a desired DNA that encodes IL-33 into a fertilized egg, unfertilized egg, spermatozoa, and precursor cell thereof (primordial germ cell, oogonium, oocyte, egg cell, spermatogonium, spermatocyte, spermatid and the like) and the like of a non-human mammal, preferably at an early stage of the embryogenesis of a fertilized egg (more preferably prior to the 8-cell stage), by a method of gene introduction such as the calcium phosphate co-precipitation method, electroporation method, lipofection method, aggregation method, microinjection method, gene gun (particle gun) method, or DEAE-dextran method. It is also possible to introduce a desired DNA into a somatic cell, tissue, organ and the like of a non-human mammal by the method of gene introduction, and to utilize them for cell culture, tissue culture and the like; furthermore, by fusing this cell with the above-described embryo (or germ) cell using a commonly known method of cell fusion, a Tg animal can also be prepared. Alternatively, as in the preparation of a knockout animal, by introducing a desired DNA into an embryonic stem cell (ES cell) of a non-human mammal with the above-described method of gene introduction, selecting a clone having the DNA integrated stably, and then injecting the ES cell into a blastocyst or allowing an ES cell mass and an 8-cell stage embryo to aggregate together, to prepare a chimeric non-human mammal, and selecting an animal having the introduced DNA transmitted to the germ line, a Tg animal can also be obtained.

A portion of the living body of a Tg animal prepared as described above (for example, (1) a cell, tissue, organ and the like that stably retain a DNA that encodes IL-33, (2) a cell or tissue derived therefrom, in culture, passaged as required, and the like) can also be used as "a portion of the living body of a non-human mammal retaining a DNA that encodes IL-33 in a specifically expressible state in the skin" of the present invention for the same purpose as that of "a non-human mammal retaining a DNA that encodes IL-33 in an expressible state" of the present invention.

Examples of preferable portions of the living body of the Tg animal of the present invention include skin, tissue section (e.g., epideimis) and cells (e.g., epidermal keratinocyte) derived from the skin, and the like.

"A non-human mammal" that can be a subject of the present invention is not particularly limited, as long as it is a non-human mammal for which a transgenic system has been established; examples include mice, bovines, monkeys, pigs, sheep, goat, rabbits, dogs, cats, guinea pigs, hamsters and the like. Mice, rabbits, dogs, cats, guinea pigs, hamsters and the like are preferable; in particular, from the viewpoint of the preparation of disease model animals, mice, which have relatively short period of ontogeny and life cycles, and which are easy to propagate (for example, C57BL/6 strain, DBA2 strain and the like as pure strains, B6C3F$_1$ strain, BDF$_1$ strain, B6D2F$_1$ strain, BALB/c strain, ICR strain and the like as hybrid strains) are preferable.

In addition to mammals, birds such as chickens can be used for the same purpose as that of "non-human mammals" being subjects of the present invention.

"A DNA that encodes IL-33" may be IL-33 derived from the non-human mammal (for example, mouse) being the subject of gene introduction, or a DNA that encodes IL-33 derived from a heterogeneous mammal (for example, humans, bovines, monkeys, pigs, sheep, goat, rabbits, dogs, cats, guinea pigs, hamsters, rats and the like) or a protein having substantially the same amino acid sequence thereas. Preferably, the DNA that encodes IL-33 of the present invention is a DNA that encodes IL-33 which is the subject of gene introduction or a protein having substantially the same amino acid sequence thereas, more preferably a DNA that encodes mouse IL-33 or a protein having substantially the same amino acid sequence thereas. A DNA that encodes mouse IL-33 includes a DNA that encodes the amino acid sequence shown by SEQ ID NO:2, preferably a DNA comprising the m base sequence shown by SEQ ID NO:1. "Substantially the same amino acid sequence" includes, in the case of mouse IL-33, for example, amino acid sequences having an identity of about 90% or more, preferably 95% or more, more preferably about 98% or more, to the amino acid sequence shown by SEQ ID NO:2, and the like. Amino acid sequence identity can be calculated using the homology calculating algorithm NCBI BLAST (National Center for Biotechnology Information Basic Local Alignment Search Tool) under the following conditions (expect=10; gap allowed; matrix=BLOSUM62; filtering=OFF).

"A protein having substantially the same amino acid sequence" is preferably, in the case of mouse IL-33, for example, a protein comprising substantially the same amino acid sequence as the amino acid sequence shown by SEQ ID NO:2, and having substantially the same quality of activity as the protein consisting of the amino acid sequence shown by SEQ ID NO:2. Examples of "substantially the same quality of activity" include (1) dermatitis induction activity, (2) induction activity on migration of inflammatory cell into dermis, (3) increasing activity on total IgE in the serum, (4) increasing activity on histamine in the plasma, (5) increasing activity on cytokine, chemokine and (6) scratching induction activity and the like. Substantially the same quality means that these activities are qualitatively equivalent. Therefore, it is preferable that the activities can be equivalent to each other, but the degrees of these activities may be different (e.g., about 0.01 to 100 times, preferably about 0.5 to 20 times, more preferably about 0.5 to 2 times). The activities can be measured according to a method known per se. They can also be measured as in the below-mentioned Examples.

The DNA that encodes IL-33 is preferably in an intron-free form (i.e., complementary DNA) like, for example, a DNA comprising the base sequence shown by SEQ ID NO:1; however, in another embodiment, an intron-containing form (i.e., genomic DNA) can also be used preferably because the 5'- and 3'-terminal sequences of introns are common to most eukaryotic genes.

The DNA that encodes IL-33 can be isolated by a hybridization method or PCR method and the like, using all or a portion of a DNA derived from a tissue of a human or various non-human mammals (bovines, monkeys, pigs, sheep, goat, rabbits, dogs, cats, guinea pigs, hamsters, rats, mice and the like) and a genomic DNA derived from a commercially available genomic DNA library as the starting material, or using a cDNA prepared by a commonly known method from an RNA derived from a tissue of a human or various non-human mammals as the starting material, using an oligonucleotide prepared on the basis of a commonly known IL-33 gene sequence as the probe or primer.

The Tg animal of the present invention retains a DNA that encodes IL-33 "in a specifically expressible state in the skin". Therefore, to introduce the DNA into a subject animal, it is generally advantageous to use the DNA in a form containing an expression cassette wherein the DNA is joined downstream of a promoter capable of specifically functioning in the skin of the subject animal (e.g., expression vector and the like).

Useful vectors for carrying a DNA that encodes IL-33 include *Escherichia coli*-derived plasmids, *Bacillus subtilis*-derived plasmids, yeast-derived plasmids, bacteriophages such as λ phage, animal or insect viruses such as retrovirus such as Moloney leukemia virus, lentivirus, adeno-associated virus, vaccinia virus and baculovirus, and the like. In particular, plasmids (preferably plasmids derived from *Escherichia coli*, *Bacillus subtilis*, or yeast, particularly plasmids derived from *Escherichia coli*) and animal viruses (preferably retrovirus, lentivirus) are preferable.

Examples of the promoter that specifically regulates the expression of IL-33 gene in the skin include promoters of genes whose expression is specifically regulated in the skin derived from various mammals (humans, bovines, monkeys, pigs, sheep, goat, rabbits, dogs, cats, guinea pigs, hamsters, rats, mice and the like) and birds (chicken and the like), preferably a promoter derived from human or mouse, more preferably a promoter derived from human. Examples of the human-derived promoter of a gene specifically regulated to be expressed in the skin include keratin promoter. Human keratin is divided into 54 kinds of subtypes, and each subtype is largely divided into Type I keratin and Type II keratin. Examples of Type I keratin include keratin 9, 10, 12-20, 23-28, 31-40, and examples of Type II keratin include keratin 1-8, 71-86. Therefore, examples of the human-derived keratin promoter include keratin 1 promoter to keratin 86 promoter. In the present invention, keratin 14 promoter (46730-47216 of GenBank AC105208.15) is preferably used. In addition, keratin 5 promoter, and a promoter contained in the ortholog of non-human mammal other than the aforementioned human keratin can also be used It is preferable that a sequence that terminates the transcription of the desired messenger RNA in the Tg animal (a polyadenylation (polyA) signal, also called a terminator) be present downstream of the DNA that encodes IL-33; for example, using a terminator sequence derived from a virus gene, or derived from a gene of various mammals or birds, efficient expression of the transgene can be achieved. Preferably, human keratin 14 polyA signal is used in the present invention. Human growth hormone polyA signal, SV40 virus polyA signal and the like can also be used. To increase the expression of IL-33, a portion of the intron of a eukaryotic gene can also be joined 5' upstream of the promoter region, between the promoter region and the coding region, or 3' downstream of the coding region. Examples of the intron sequence used in this case include rabbit β globin intron 2 and the like. Chimera intron of rabbit β globin and IgG, CMV intron, SV40 intron and the like can also be used. The splicing signal of each gene, and an enhancer region can also be joined at the 5' upstream of the promoter region, between the promoter region and the coding region, or the 3' downstream of the coding region.

When a Tg animal is prepared using an embryonic stem cell (ES cell), the above-described vector preferably further comprises a selection marker gene (e.g., drug resistance genes such as neomycin resistance gene and hygromycin resistance gene) for selecting a clone having the introduced DNA stably integrated therein.

The above-described promoter, intron, DNA encoding IL-33, polyA signal and the like can be inserted into the above-described vector in the right arrangement, i.e., in an arrangement that allows the specific expression of IL-33 in the skin of Tg animal, by an ordinary gene engineering technique using an appropriate restriction enzyme and DNA ligase and the like. For example, as used in the below-mentioned Examples, keratin promoter, intron, DNA encoding IL-33, and polyA signal are preferably linked in this order from the 5'-side. More preferably, keratin 14 promoter, rabbit β globin intron 2, DNA encoding IL-33 having a base sequence of SEQ ID NO: 1 and human keratin 14 polyA signal are linked in this order from the 5'-side in a vector.

In a preferred embodiment, the expression vector comprising a DNA that encodes IL-33, obtained as described above, is introduced to an early embryo of a non-human mammal being the subject by microinjection.

An early embryo of the subject non-human mammal can be obtained by collecting an in vivo fertilized egg obtained by mating a male and female non-human mammal of the same species, or by in vitro fertilization of an ovum and spermatozoa respectively collected from a female and male non-human mammal of the same species.

The age, rearing conditions and the like of the non-human mammal used vary depending on animal species; for example, when a mouse (preferably, a mouse of an inbred strain such as C57BL/6J(B6), $F_1$ of B6 and another inbred strain, and the like) is used, it is preferable that a female at about 4 to about 6 week-old and a male at about 2 to about 8 month-old be used, and that the mice be reared with a light period of about 12 hours per day (for example, 7:00-19:00) for about 1 week.

Although the in vivo fertilization may be by natural mating, a method is preferable comprising administering a gonadotropic hormone to a female non-human mammal to induce overovulation, and then mating the female with a male non-human mammal, for the purpose of adjusting the estrous cycle and obtaining a large number of early embryos from a single individual. For inducing ovulation in a female non-human mammal, for example, a method is preferable comprising administering a follicle-stimulating hormone (pregnant mare serum gonadotropin, generally abbreviated as PMSG), and then a luteinizing hormone (human chorionic gonadotropin, generally abbreviated as hCG), by, for example, intraperitoneal injection and the like; preferable amounts and frequencies of administration of the hormones vary depending on the species of the non-human mammal. For example, when the non-human mammal is a mouse (preferably, a mouse of an inbred strain such as C57BL/6J (B6), $F_1$ of B6 and another inbred strain, and the like), generally a method is preferable comprising administering a follicle-stimulating hormone, then administering a luteinizing hormone about 48 hours later, and immediately mating the female mouse with a male mouse to obtain a fertilized egg, wherein the amount of the follicle-stimulating hormone administered is about 20 to about 50 IU/individual, preferably about 30 IU/individual, and the amount of the luteinizing hormone administered is about 0 to about 10 IU/individual, preferably about 5 IU/individual.

After elapse of a given time, a female non-human mammal confirmed to have copulated by vaginal plug examination and the like is laparotomized, a fertilized egg is removed from the oviduct, washed in a medium for embryo culture (e.g., M16 medium, modified Whitten medium, BWW medium, M2 medium, WM-HEPES medium, BWW-HEPES medium and the like) to remove cumulus oophorus cells, and cultured in 5% gaseous carbon dioxide/95% air by the microdrop culture method and the like until DNA microinjection. If microinjection is not immediately performed, the fertilized egg collected may be stored under freezing by the slow method or the ultrarapid method and the like.

Meanwhile, in the case of in vitro fertilization, a follicle-stimulating hormone and a luteinizing hormone are administered to a female non-human mammal for egg collection (the same as in in vivo fertilization is preferably used) as described above to induce ovulation, after which ova are collected and cultured in a medium for fertilization (e.g., TYH medium) in 5% gaseous carbon dioxide/95% air by the microdrop culture method and the like until in vitro fertilization. Separately, the cauda epididymidis is removed from a male non-human mammal of the same species (the same as in in vivo fertilization is preferably used), and a spermatozoa mass is collected and precultured in a medium for fertilization. After completion of the preculture, spermatozoa are, added to the medium for fertilization containing the ova, and the ova are cultured in 5% gaseous carbon dioxide/95% air by the microdrop culture method and the like, after which a fertilized egg having two pronuclei is selected under a microscope. If DNA microinjection is not immediately performed, the fertilized egg obtained may be stored under freezing by the slow method or the ultrarapid method and the like.

DNA microinjection into the fertilized egg can be performed by a conventional method using a commonly known device such as a micromanipulator. Briefly, the fertilized egg placed in a microdrop of a medium for embryo culture is aspirated and immobilized using a holding pipette, and a DNA solution is injected directly into the male or female pronucleus, preferably into the male pronucleus, using an injection pipette. The introduced DNA is used preferably after being highly purified using CsCl density gradient ultracentrifugation or an anion exchange resin column and the like. It is also preferable that the introduced DNA be linearized in advance by cutting the vector portion using a restriction enzyme.

After introducing the DNA, the fertilized egg is cultured in a medium for embryo culture in 5% gaseous carbon dioxide/95% air by the microdrop culture method and the like until the 1-cell stage to blastocyst stage, after which it is transplanted to the oviduct or uterus of a pseudopregnant embryo recipient female non-human mammal. The embryo recipient female non-human mammal for embryo reception may be any one of the same species as the animal from which the early embryo to be transplanted is derived; for example, when a mouse early embryo is transplanted, a female ICR mouse (preferably about 8 to about 10 week-old) and the like are preferably used. A known method of rendering an embryo recipient female non-human mammal pseudopregnant is, for example, a method comprising mating the female with a vasectomized (vasoligated) male non-human mammal of the same species (for example, in the case of a mouse, with a male ICR mouse (preferably about 2 month-old or more)), and selecting a female confirmed to have a vaginal plug.

The embryo recipient female used may be one that has ovulated naturally, or one receiving luteinizing hormone releasing hormone (generally abbreviated LHRH) or an analogue thereof administered prior to mating with a vasectomized (vasoligated) male, to induce fertility. Examples of the LHRH analogue include[3,5-DiI-Tyr$^5$]-LH-RH, [Gln$^8$]-LH-RH, [D-Ala$^6$]-LH-RH, [des-Gly$^{10}$]-LH-RH, [D-His(Bzl)$^6$]-LH-RH and Ethylamides thereof and the like. The amount of LHRH or an analogue thereof administered, and the timing of mating with a male non-human mammal after the administration vary depending on the species of the non-human mammal. For example, when the non-human mammal is a mouse (preferably an ICR mouse and the like), it is usually preferable that the female mouse be mated with a male mouse about 4 days after administration of LHRH or an analogue thereof; the amount of LHRH or an analogue thereof administered is usually about 10 to 60 μg/individual, preferably about 40 μg/individual.

Usually, when the early embryo to be transplanted is in the morula stage or after, the embryo is transplanted to the uterus of an embryo recipient female; when the early embryo is in a stage before the morula stage (for example, 1-cell stage 30 to 8-cell stage embryo), the embryo is transplanted to the oviduct. The female for embryo reception is used as appropriate after elapse of a given number of days after becoming pseudopregnant depending on the developmental stage of the embryo to be transplanted. For example, in the case of a mouse, a female mouse at about 0.5 days after becoming pseudopregnant is preferable for the transplantation of a 2-cell stage embryo, and a female mouse at about 2.5 days after becoming pseudopregnant is preferable for the transplantation of a blastocystic embryo. After the embryo recipient female is anesthetized (preferably, Avertin, Nembutal and the like are used), an incision is made, the ovary is pulled out, and early embryos (about 5 to about 10 embryos) in suspension in a medium for embryo culture are injected into the vicinity of the abdominal osteum of the uterine tube or the uterine tube junction of the uterine horn using a pipette for embryo transplantation.

When the transplanted embryo implants successfully and the embryo recipient female becomes pregnant, non-human mammal pups will be obtained by natural delivery or caesarean section. Embryo recipient females that have delivered naturally are allowed to continue suckling; if the pups are delivered by caesarean section, the pups can be suckled by a separately provided female for suckling (for example, in the case of the mouse, a female mouse with usual mating and delivery (preferably a female ICR mouse and the like)).

Introduction of the DNA that encodes IL-33 at the fertilized egg cell stage is secured so that the introduced DNA will be present in all of the germline cells and somatic cells of the subject non-human mammal. Whether or not the introduced DNA is integrated into chromosome DNA can be determined by, for example, screening chromosome DNAs separated and extracted from the tail of the pup, by Southern hybridization or PCR. The presence of a DNA that encodes IL-33 in the germline cells of the offspring non-human mammal ($F_0$) obtained as described above means that the DNA that encodes IL-33 is present in all of the germline cells and somatic cells of all animals in the subsequent generation ($F_1$).

Generally, $F_0$ animals are obtained as heterozygotes having the introduced DNA in either one of the homologous chromosomes. Different $F_0$ individuals have the introduced DNA inserted randomly into different chromosomes unless the insertion is by homologous recombination. To obtain a homozygote having the DNA that encodes IL-33 in both of the homologous chromosomes, an $F_0$ animal and a non-transgenic animal are crossed to prepare an $F_1$ animal, and heterozygous siblings thereof having the introduced DNA in either one of the homologous chromosomes may be crossed. If the introduced DNA is integrated only at one gene locus, ¼ of the $F_2$ animals obtained will be homozygotes.

In another embodiment, an expression vector comprising a DNA that encodes IL-33 is introduced into an ES cell of the non-human mammal being the subject by a commonly known method of gene introduction such as electroporation.

An ES cell refers to a cell derived from an inner cell mass (ICM) of a fertilized egg in the blastocyst stage, and can be cultivated and maintained while keeping the undifferentiated state in vitro. ICM cells are destined to form the embryo body, being stem cells on which all tissues, including germ cells, are based. The ES cell used may be of an established cell line, or of a cell line newly established in accordance with the method of Evans and Kaufman (Nature, vol. 292, p. 154, 1981). For example, in the case of mouse ES cells, ES cells derived from a 129 strain mouse are currently generally used, but the immunological background thereof is unclear; for the purposes of acquiring ES cells of a pure strain instead thereof with an immunologically clear genetic background and the like, an ES cell established from a C57BL/6 mouse or from a BDF$_1$ mouse (F$_1$ of C57BL/6 and DBA/2), wherein the small number of ova collectable from C57BL/6 has been improved by crossing with DBA/2, and the like can also be used suitably. In addition to being advantageous in that the number of ova collectable is high, and that the ova are robust, BDF$_1$ mice have the C57BL/6 mouse as the background thereof; therefore, ES cells derived therefrom can be used advantageously in that, when preparing a disease model mouse, the genetic background can be replaced with that of the C57BL/6 mouse by back-crossing with a C57BL/6 mouse.

ES cells can be prepared by, for example, as described below. When a blastocystic embryo is collected from the uterus of a female non-human mammal [for example, when a mouse (preferably a mouse of an inbred strain such as C57BL/6J(B6), F$_1$ of B6 and another inbred strain, and the like) is used, a female mouse at about 8 to about 10 week-old (about 3.5 days of gestation) mated with a male mouse at about 2 month-old or more is preferably used] (or an early embryo in the morula stage or before is collected from the oviduct, after which it may be cultured in a medium for embryo culture as described above until the blastocyst stage), and cultured on a layer of appropriate feeder cells (for example, in the case of a mouse, primary fibroblasts prepared from a fetal mouse, commonly known STO fibroblast line and the like), some cells of the blastocyst gather to form an ICM that will differentiate into an embryo. This inner cell mass is trypsinized to dissociate single cells, and while maintaining an appropriate cell density and making medium exchanges, dissociation and passage are repeated, whereby ES cells are obtained.

Although both male and female ES cells can be used, male ES cells are usually more convenient in preparing a germline chimera. Also for the sake of saving painstaking labor for cultivation, it is desirable that sex identification be performed as early as possible. An example of the method of identifying the sex of an ES cell is a method comprising amplifying and detecting a gene in the sex determining region on Y chromosome by PCR. Using this method, about 1 colony of ES cells (about 50 cells) is sufficient, compared to the conventional method, which requires about $10^6$ cells for karyotype analysis, so that primary selection of ES cells in early stages of cultivation can be performed by sex identification, thus making early selection of male cells possible, whereby labor in early stages of cultivation can be reduced significantly.

Secondary selection can be performed by, for example, confirming chromosome numbers by the G-banding method, and the like. It is desirable that the chromosome number of the ES cell obtained be 100% of the normal number; however, if this is difficult to achieve because of physical operations in establishing the cell line and the like, it is desirable that after gene introduction into the ES cell, the gene be recloned into a normal cell (for example, in the case of a mouse, a cell whose chromosome number is 2n=40).

The ES cell line thus obtained needs to be subcultured carefully to maintain the nature of undifferentiated stem cells. For example, the ES cell line is cultured by, for example, a method comprising culturing on appropriate feeder cells, like STO fibroblasts, in the presence of LIF (1 to 10,000 U/ml), known as a differentiation suppressing factor, in a gaseous carbon dioxide incubator (preferably, 5% gaseous carbon dioxide/95% air or 5% oxygen/5% gaseous carbon dioxide/90% air) at about 37° C., and the like; upon passage, for example, the ES cell line is treated with trypsin/EDTA solution (usually 0.001 to 0.5% trypsin/0.1 to 5 mM EDTA, preferably about 0.1% trypsin/1 mM EDTA) to obtain single cells, which are sown onto freshly prepared feeder cells, and the like. This passage is normally performed every 1 to 3 days, during which the cells were examined; if a morphologically abnormal cell is found, it is desirable that the cultured cells be discarded.

ES cells can be differentiated into a wide variety of types of cell, including parietal muscle, visceral muscles, and cardiac muscle, by monolayer culture until the reach of a high density, or suspension culture until the formation of cell aggregates, under appropriate conditions [M. J. Evans and M. H. Kaufman, Nature vol. 292, p. 154, 1981; G. R. Martin, Proceedings of the National Academy of Sciences, USA (Proc. Natl. Acad. Sci. U.S.A.), vol. 78, p. 7634, 1981; T. C. Doetschman et al., Journal of Embryology and Experimental Morphology, vol. 87, p. 27, 1985]; the non-human mammal cells specifically expressing IL-33 in the skin according to the present invention, which are obtained by differentiating an ES cell incorporating a DNA that encodes IL-33, are useful in cell biological investigations of IL-33 in vivo.

Although any of the calcium phosphate co-precipitation method, electroporation method, lipofection method, retrovirus infection method, aggregation method, microinjection method, gene gun (particle gun) method, DEAE-dextran method and the like can be used for gene introduction into ES cells, the electroporation method is generally chosen because of the ease of treatment of a large number of cells and the like. For the electroporation, ordinary conditions used for gene introduction into animal cells may be used as is; for example, the electroporation can be performed by trypsinizing ES cells in the logarithmic growth phase to disperse them as single cells, suspending the cells in a medium to obtain a density of $10^6$ to $10^8$ cells/ml, transferring the cells to a cuvette, adding 10 to 100 μg of a vector comprising a DNA that encodes IL-33, and applying an electric pulse of 200 to 600 V/cm.

ES cells having the introduced DNA integrated therein can be determined by screening chromosome DNA separated and extracted from a colony obtained by culturing the single cells on feeder cells, by Southern hybridization or PCR; the biggest feature of transgenic systems using ES cells resides in the fact that transformants can be selected at the cell level with the expression of a drug resistance gene or a reporter gene as the index. Therefore, the introduction vector used here desirably further comprises, in addition to an expression cassette comprising a DNA that encodes IL-33, a selection marker gene such as a drug resistance gene (e.g., neomycin phosphotransferase II (nptII) gene, hygromycin phosphotransferase (hpt) gene and the like) or a reporter gene (e.g., β-galactosidase (lacZ) gene, chloramphenicol acetyltransferase (cat) gene and the like). For example, when to a vector comprising the nptII gene as the selection marker gene is used, ES cells after gene introduction treatment are cultured in a medium containing a neomycin-series antibiotic such as G418, the resulting resistant colonies are transferred to respective culture plates, and trypsinization and medium exchanges are repeated, after which a portion is reserved for cultivation, and the remainder is subjected to PCR or Southern hybridization to confirm the presence of the introduced DNA.

When an ES cell confirmed to have the introduced DNA integrated therein is returned to an embryo derived from a non-human mammal of the same species, the ES cell gets integrated into the ICM of the host embryo to form a chimeric embryo. This is transplanted into a recipient mother (embryo recipient female) and allowed to continue development, whereby a chimeric transgenic animal is obtained. If the ES cell contributes to the formation of a primordial germ cell that will differentiate into an egg or spermatozoon in the chimera animal, a germline chimera will be obtained; by mating this, a Tg animal having the introduced DNA maintained genetically therein can be prepared.

For preparing a chimeric embryo, there are a method wherein early embryos up to the morula stage are adhered and aggregated together (aggregation chimera method) and a method wherein a cell is micro-injected into a blastocoel cavity of a blastocyst (injection chimera method). Although the latter has traditionally been widely conducted in the preparation of a chimeric embryo using an ES cell, a method wherein an aggregation chimera is created by injecting an ES cell into the zona pellucida of an 8-cell stage embryo, and a method wherein an aggregation chimera is created by co-culturing and aggregating an ES cell mass and an 8-cell stage embryo deprived of the zona pellucida, as a method which does not require a micromanipulator and which can be easily operated, have recently been conducted.

In all cases, a host embryo can be collected from a non-human mammal that can be used as a female for egg collection in gene introduction into a fertilized egg in the same manner; for example, in the case of a mouse, to make it possible to determine the percent contribution of ES cells to the formation of a chimera mouse by coat color, it is preferable that the host embryo be collected from a mouse of a strain showing a coat color different from that of the strain from which the ES cell is derived. For example, in the case of an ES cell derived from a 129 strain mouse (coat color: agouti), a C57BL/6 mouse (coat color: black) or an ICR mouse (coat color: albino) is used as the female for egg collection; in the case of an ES cell derived from a C57BL/6 or $DBF_1$ mouse (coat color: black) or from a TT2 cell (derived from F$_1$ (coat color: agouti) of C57BL/6 and CBA), an ICR mouse or a BALB/c mouse (coat color: albino) can be used as the female for egg collection.

Because the germline chimera formation capacity depends largely on the combination of an ES cell and a host embryo, it is more preferable that a combination showing a high germline chimera formation capacity be chosen. For example, in the case of a mouse, it is preferable to use a host embryo derived from the C57BL/6 strain and the like for ES cells derived from the 129 strain, and to use a host embryo derived from the BALE/c strain and the like for ES cells derived from the C57BL/6 strain.

It is preferable that the female mouse for egg collection be about 4 to about 6 week-old, and that the male mouse for mating be of the same strain at about 2 to about 8 month-old. Although the mating may be by natural mating, it is preferably performed after administering gonadotropic hormones (follicle-stimulating hormone, then luteinizing hormone) to induce overovulation.

In the case of the blastodisk injection method, a blastocystic embryo (for example, in the case of a mouse, at about 3.5 days after mating) is collected from the uterus of a female for egg collection (or an early embryo in the morula stage or before, after being collected from the oviduct, may be cultured in the above-described medium for embryo culture until the blastocyst stage), and ES cells (about 10 to about 15 cells) having a DNA that encodes IL-33 introduced thereinto are injected into a blastocoel cavity of the blastocyst using a micromanipulator, after which the embryos are transplanted into the uterus of a pseudopregnant embryo recipient female non-human mammal. As the embryo recipient female non-human mammal, a non-human mammal that can be used as an embryo recipient female in gene introduction into a fertilized egg can be used in the same manner.

In the case of the co-culture method, 8-cell stage embryos and morulas (for example, in the case of a mouse, about 2.5 days after mating) are collected from the oviduct and uterus of a female for egg collection (or an early embryo in the 8-cell stage or before, after being collected from the oviduct, may be cultured in the above-described medium for embryo culture until the 8-cell stage or morula stage), and the zona pellucida is lysed in acidic Tyrode's solution, after which an ES cell mass incorporating a DNA that encodes IL-33 (number of cells: about 10 to about 15 cells) is placed in a microdrop of a medium for embryo culture overlaid with mineral oil, the above-described 8-cell stage embryo or morula (preferably 2 embryos) is further placed, and they are co-cultured overnight. The morula or blastocyst obtained is transplanted to the uterus of an embryo recipient female non-human mammal as described above.

When the transplanted embryo implants successfully and the embryo recipient female becomes pregnant, chimeric non-human mammal pups will be obtained by natural delivery or caesarean section. Embryo recipient females that have delivered spontaneously are allowed to continue suckling; if the pups are delivered by caesarean section, the pups can be suckled by a separately provided female for suckling (a female non-human mammal with usual mating and delivery).

For the selection of a germline chimera, if the sex of the ES cell has already been determined, a chimera mouse of the same sex as the ES cell first is selected (usually, a male chimera mouse is chosen since a male ES cell is used), and then a chimera mouse showing a high ES cell contribution rate (for example, 50% or more) is selected on the basis of phenotypes such as coat color. For example, in the case of a chimera mouse obtained from a chimera embryo between a D3 cell, which is a male ES cell derived from a 129 strain mouse, and a host embryo derived from a C57BL/6 mouse, it is preferable that a male mouse showing a high percentage of the agouti coat color be selected. Whether or not the selected chimera non-human mammal is a germline chimera can be determined on the basis of the phenotypes of the F$_1$ animal obtained by crossing with an appropriate strain of the same animal species. For example, in the case of the above-described chimera mouse, agouti is dominant over black; therefore, when the male mouse is crossed with a female C57BL/6 mouse, the coat color of the F$_1$ obtained is agouti if the selected male mouse is a germline chimera.

The thus-obtained germline chimera non-human mammal incorporating a DNA that encodes IL-33 (founder) is usually obtained as a heterozygote having the introduced DNA in either one of the homologous chromosomes. Individual founders have the introduced DNA inserted randomly into different chromosomes unless the insertion is by homologous recombination. To obtain a homozygote having a DNA that encodes IL-33 in both homologous chromosomes, of the F$_1$ animals obtained as described above, siblings of heterozygotes having the introduced DNA in either one of the homologous chromosomes may be crossed. Selection of heterozygotes can be determined by, for example, screening chromosome DNAs separated and extracted from the tail of an F$_1$ animal by Southern hybridization or PCR. If the introduced DNA is integrated only at one gene locus, ¼ of the F$_2$ animals obtained will be homozygotes.

Another preferred embodiment with the use of a virus as the expression vector is a method comprising infecting an early embryo or ES cell of a non-human mammal with a virus comprising a DNA that encodes IL-33 (see, for example, Proceedings of the National Academy of Sciences, USA (Proc. Natl. Acad. Sci. USA), vol. 99, No. 4, pp. 2140-2145, 2002). For example, when retrovirus or lentivirus is used, cells (fertilized eggs preferably deprived of the zona pellucida) are sown to an appropriate incubator such as a culture dish, a virus vector is added to the culture broth (if desired, polybrene may be co-present), the cells are cultured for 1 to 2 days, after which, in the case of an early embryo, the embryo is transferred to the oviduct or uterus of a pseudopregnant embryo recipient female non-human mammal as described above, or in the case of an ES cell, a selection drug such as G418 or hygromycin is added and cultivation is continued as described above, and cells having the vector integrated therein are selected.

Furthermore, as described in the Proceedings of the National Academy of Sciences, USA (Proc. Natl. Acad. Sci. USA), vol. 98, pp. 13090-13095, 2001, a spermatogonium collected from a male non-human mammal is infected with a virus vector during co-cultivation with STO feeder cells, after which the spermatogonium is injected into the seminiferous tube of a male infertile non-human mammal, and the male infertile non-human mammal is mated with a female non-human mammal, whereby IL-33 hetero-Tg (+/−) pups can be obtained efficiently.

The Tg animal of the present invention is characterized in that it has one or more features selected from the group consisting of the following:
(1) spontaneous onset of dermatitis,
(2) increase in the number of inflammatory cells,
(3) increase in total IgE concentration, histamine concentration, cytokine concentration and/or chemokine concentration, and
(4) increase in scratching time, under SPF (specific pathogen free) breeding conditions, as compared to a corresponding non-transgenic non-human mammal.

Atopic dermatitis patients show higher expression intensity of IL-33 in epidermal keratinocyte than said cells of healthy human (non-patent document 3). In addition, IL-5 gene expression is promoted in a rash site of human atopic dermatitis patients (Corren J, Discov Med 13:305-12, 2012), and even patients free of an increase in eosinophils in blood show eosinophil infiltration in a rash site (Kiehl P et al., Br J Dermatol. 145:720-9, 2001). Furthermore, atopic dermatitis patients show an increase in the histamine concentration and IgE concentration along with the activation of mast cells.

On the other hand, the above-mentioned Tg animal of the present invention can also confirm remarkably high levels of IL-33 expression in the skin, and the phenotype thereof also matches the features of atopic dermatitis patients. In the below-mentioned Examples, when the Tg animal of the present invention is Tg mouse, a part of the Tg mice developed dermatitis from 6 weeks of age under SPF breeding conditions, and all Tg mice spontaneously developed dermatitis from 8 weeks of age and thereafter. Also, inflammatory cells (particularly eosinophils, mast cells, type 2 innate lymphoid cells) significantly increased in the skin, peripheral blood or lymph node. Furthermore, total IgE concentration in the serum also increased significantly as compared to wild-type mice, and histamine concentration in the plasma also increased significantly as compared to wild-type mice. As cytokine, IL-4, IL-13 significantly increased in the skin, and IL-5 significantly increased in the skin and serum as compared to wild-type mice. As chemokine, CCL5, CCL11 significantly increased in the skin and CCL2, CCL4 significantly increased in the skin and serum as compared to wild-type mice. In addition, the scratching time significantly increased as compared to wild-type mice, and anti-histamine drugs (diphenhydramine hydrochloride) and steroid drugs (betamethasonebutyric acid ester propionic acid ester) could reduce the increased scratching time and rash score.

More specifically, the aforementioned feature of Tg mice of the present invention as shown by the rash score of dermatitis was about 10-15. The number of inflammatory cells was about 7- to 8-fold in the skin, about 4- to 5-fold in the peripheral blood in the case of eosinophils, about 2- to 3-fold in the skin in the case of mast cells, and about 12-fold in the skin, about 10-fold in the peripheral blood, and about 20-fold in the lymph node, in the case of type 2 innate lymphoid cells, as compared to wild-type mice. The total IgE concentration was about 20- to 30-fold as compared to wild-type mice, and the histamine concentration was about 8- to 9-fold as compared to wild-type mice. The cytokine concentration of IL-4, IL-13 increased to about 50-fold, about 3-fold in the skin and IL-5 was about 50-fold, about 1500-fold or more in the skin and serum, respectively (IL-5 in the serum was not more than marginal (0.3 pg/mL) in wild-type but about 500 pg/mL in Tg mice) as compared to wild-type mice. In addition, CCL5, CCL11 increased to about 4-fold, about 5-fold, respectively, in the skin, CCL2 increased to about 7-fold and about 14-fold in the skin and serum, respectively, and CCL4 increased to about 8-fold and about 100-fold in the skin and serum, respectively.

From the above features, it is considered that, in the Tg animal of the present invention, under control of human keratin 14 promoter, a DNA encoding IL-33 is skin-specifically highly expressed, induces inflammation reaction via activation of eosinophils, mast cells, type 2 innate lymphoid cells, and develop atopic dermatitis.

Therefore, the Tg animal of the present invention is useful for screening for a prophylactic or therapeutic drug for atopic dermatitis, and the present invention provides a method of screening for a therapeutic agent for atopic dermatitis, comprising, under SPF (specific pathogen free) breeding conditions, applying a test compound to the TG animal, and measuring one or more items selected from the group consisting of (1) rash score, (2) number of inflammatory cells, (3) total IgE concentration, histamine concentration, cytokine concentration and/or chemokine concentration, and (4) scratching time, and selecting a test substance that improves the aforementioned measured item as compared to non-administration of the test compound.

In the screening method of the present invention, a test compound is administered to the Tg animal of the present invention. Examples of the test compound to be used include, in addition to commonly known synthetic compounds, peptides, proteins, DNA libraries and the like, for example, tissue extracts, cell culture supernatants and the like of mammals (for example, mice, rats, pigs, bovines, sheep, monkeys, humans and the like). The timing of administration of the test compound may be before or after observation of the aforementioned features. The administration method may be oral or parenteral. For oral administration, a test compound may be mixed with feed or drink water and administered. For parenteral administration, administration by coating, intraperitoneal administration, administration by intravenous injection, subcutaneous injection, intradermal injection, intramuscular injection, drip injection and the like, rectal administration by suppository and the like can be mentioned. The administration may be single administration or multiple administrations.

Each item can be measured by a known method, or according to the below-mentioned Examples. For example, as for the rash score, 5 items of pruritus, erythematous plaque/bleeding, edema, epidermis detachment/erosion, and desquamation/drying are evaluated and rated as absent (0 point), mild (1 point), moderate (2 points), and severe (3 points), and the total points are used for measurement (Matsuda H et al., Int. Immunol, 9(3):461-466, 1997). As for the number of inflammatory cells, for example, cells derived from skin tissue, peripheral blood or lymph node are analyzed by flow cytometry, and the ratio thereof can be measured. The inflammatory cells include eosinophils, neutrophils, basophils, mast cells, type 2 innate lymphoid cells and the like, preferably eosinophils, mast cells and type 2 innate lymphoid cells. The total IgE concentration, histamine concentration, cytokine concentration and chemokine concentration can be measured by ELISA using each antibody. As used herein, cytokine is preferably IL-5 or IL-13. The scratching time can be obtained by measuring the scratching time within a given time after administration of a test compound.

The measurement results of the aforementioned features obtained as mentioned above are compared with those of non-administration of the test compound. When the obtained measurement results of the aforementioned features have been improved from those of non-administration of the test compound, the test compound can be selected as a prophylactic or therapeutic drug for atopic dermatitis. Here, being improved means (1) rash score becomes lower than that of non-administration of the test compound, (2) number of inflammatory cells becomes lower than that of non-administration of the test compound, (3) total IgE concentration, histamine concentration, cytokine concentration and/or chemokine concentration become(s) lower than that of non-administration of the test compound, or (4) scratching time becomes shorter than that of non-administration of the test compound. For example, when the measurement results after administration of a test compound are that (1) rash score decreases by not less than 60%, preferably not less than 70%, (2) number of inflammatory cells decreases by not less than 65%, preferably not less than 75%, more preferably not less than 85%, (3) total IgE concentration decreases by not less than 65%, preferably not less than 75%, more preferably not less than 85%, histamine concentration decreases by not less than 85%, preferably not less than 90%, cytokine concentration decreases by not less than 70%, preferably not less than 80%, chemokine concentration decreases by not less than 70%, preferably not less than 80%, and/or (4) scratching time decreases by not less than 70%, preferably not less than 80%, as compared to those of non-administration of the test compound, the test compound can be selected as a prophylactic or therapeutic drug for atopic dermatitis.

Alternatively, a correlation chart between the aforementioned features and the presence or absence of atopic dermatitis is prepared in advance, the obtained measurement results of the aforementioned features may be compared with the correlation chart. Comparison is preferably made based on the presence or absence of a significant difference. When the compared results show improvement from those of non-administration of the test compound, the test compound can be selected as a prophylactic or therapeutic drug for atopic dermatitis.

A therapeutic agent for atopic dermatitis selected by the screening method can be used for the improvement of symptoms of atopic dermatitis in mammals (preferably human). The therapeutic drug is prepared as a pharmaceutical preparation as necessary, and can be administered orally or parenterally to mammals (e.g., human, rat, mouse, guinea pig, rabbit, sheep, swine, bovine, horse, cat, dog, monkey and the like).

The dose of the prophylactic or therapeutic drug for atopic dermatitis varies depending on the age and body weight of the administration subject, severity of symptom, administration route and the like. When, for example, it is applied to the skin, the dose for an adult (body weight 60 kg) is generally about 0.1 mg to about 100 mg, preferably about 1.0 to about 50 mg, more preferably about 1.0 to about 20 mg, per day. When the administration subject is a non-human animal, an amount corresponding to that of 60 kg body weight can be administered.

Since the Tg animal of the present invention is useful as an animal model of atopic dermatitis, the animal can be used for an evaluation method of a prophylactic or therapeutic drug for atopic dermatitis. Therefore, the present invention provides a method of evaluating an effect of a prophylactic or therapeutic drug for atopic dermatitis, comprising, under SPF (specific pathogen free) breeding conditions, applying a prophylactic or therapeutic drug for atopic dermatitis to the Tg animal, and measuring one or more items selected from the group consisting of (1) rash score, (2) number of inflammatory cells, (3) total IgE concentration, histamine concentration, cytokine concentration and/or chemokine concentration, and (4) scratching time, and comparing the aforementioned measured item with non-administration of the prophylactic or therapeutic drug for atopic dermatitis.

The prophylactic or therapeutic drug for atopic dermatitis to be administered to the Tg animal of the present invention in the evaluation method of the present invention may be a known prophylactic or therapeutic agent and examples thereof include, but are not limited to, steroids (adrenal cortex hormone) (e.g., clobetasol propionate, betamethasone butyrate propionate, beclometasone dipropionate, alclometasone dipropionate, dexamethasone acetate and the like); tacrolimus external medicine (protopic (registered trade mark) ointment); anti-histamine drugs (e.g., diphenhydramine hydrochloride, chlorpheniramine maleate, promethazine hydrochloride, hydroxyzine, cyproheptadine hydrochloride, epinastine hydrochloride etc.) and the like. The administration period, administration method, administration frequency and the like of the prophylactic or therapeutic drug for atopic dermatitis may be the same as those of the aforementioned screening method. The dose can be appropriately determined by those of ordinary skill in the art according to each prophylactic or therapeutic drug for atopic dermatitis.

The measurement methods of the features to be compared in the evaluation method of the present invention can be performed according to the description of the aforementioned screening method. When the measurement results of the aforementioned features obtained in the evaluation method are greatly improved from those of non-administration of the prophylactic or therapeutic drug for atopic dermatitis, the prophylactic or therapeutic drug for atopic dermatitis can be evaluated to have a high prophylactic or therapeutic effect. Here, being improved means the same as above.

EXAMPLES

The present invention is hereinafter described in more detail by means of the following Examples, which, however, are not to be construed as limiting the scope of the invention.

Example 1

Construction of Transgene

A K14 expression vector containing, between EcoRI and HindIII sites of pBluescript II KS(−) phagemid vector (Agilent technologies, La Jolla, Calif.), a DNA sequence containing a 2.0 kb human keratin 14 promoter (base sequence 40251-42254 of GenBank AC105208.15), a DNA sequence containing 0.64 kb rabbit β globin intron 2 (551-1195 of GenBank V00878.1), and a DNA sequence containing 0.49 kb human keratin 14 poly A signal (46730-47216 of GenBank AC105208.15) was produced. This vector has a construction wherein BamHI site is disposed between rabbit β globin intron 2 and human keratin 14 poly A signal, and cDNA inserted into BamHI site is stably expressed in stratified squamous epithelia such as epidermis and the like under the control of keratin 14 promoter. cDNA (61-861 base sequence of GenBank AK163464.1) encoding 0.8 kb full length mouse IL-33 variant 1 was amplified using plasmid DNA contained in Fantom™ clone B230120N24 (dnaform, Yokohama) as a template, and PCR primers of

```
mIL33cinf1:
                                      (SEQ ID NO: 3)
5'-GGGCGAATACGGATCATGAGACCTAGAATGAAGTATTCCA-3'
and mIL33cinf2:
                                      (SEQ ID NO: 4)
5'-GGACTCTAGAGGATCTTAGATTTTCGAGAGCTTAAACATA-3'
``` and inserted into the BamHI site by using In-Fusion HD cloning kit (Takara Bio Inc., Otsu). The obtained mouse IL-33 cDNA expression vector was digested with restriction enzymes XmaI, XhoI, XmnI, and 4.0 kb linear DNA containing human keratin 14 promoter, rabbit β globin intron 2, mouse IL-33 variant 1 cDNA, and human keratin 14 poly A signal was isolated and purified (FIG. 1).

Example 2

Preparation of IL-33 Gene Transgenic Mice

Preparation of transgenic mice by microinjection was performed in accordance with the method of Hogan et al. (Manipulating the mouse embryo, Cold Spring Harbor Laboratory Press, 1994). The aforementioned DNA fragment containing mouse IL-33 variant 1 cDNA, prepared in Example 1, was microinjected into the pronuclei of 400 fertilized eggs derived from C57BL/6J lineage. The fertilized egg receiving the injection was tubally transplanted to a pseudopregnant female mice, and the mice were reared. The obtained 122 babies were weaned at 4 weeks of age. When they reached 6-week-old, DNA was collected from the tail of 109 mice that grew (male 68, female 41). The obtained DNA was subjected to PCR using a primer set having the sequences of

```
msF4358:
5'-GGAGGGGGCAAAGTTTTCAGGGTG-3'    (SEQ ID NO: 5)
and mIL33R5046:
5'-TTTGCAAGGCGGGACCAGGG-3',       (SEQ ID NO: 6)
``` whereby 12 mice were confirmed to have a transgene.

Example 3

Analysis of IL-33 Gene Expression in Ear Tissue of IL-33 Gene Transgenic Mice

Figure 2:
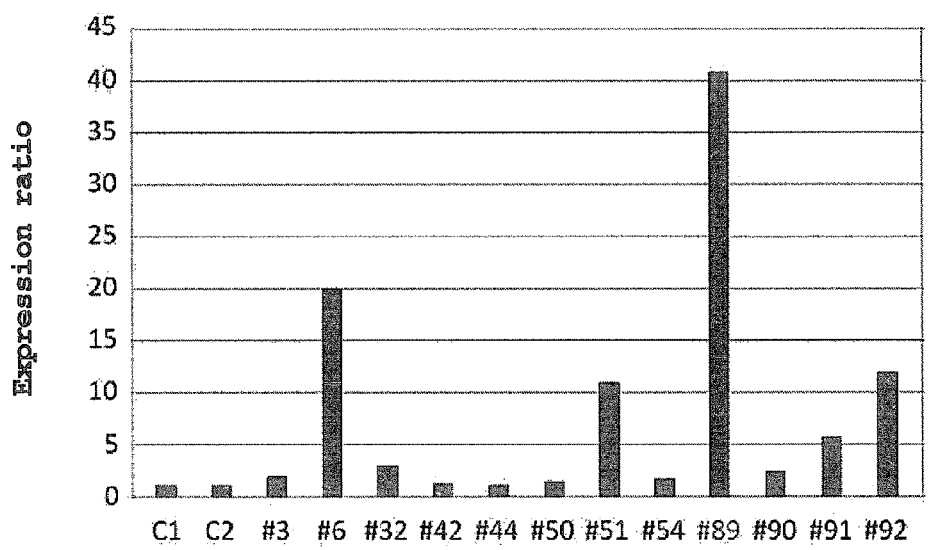
FIG. 2 shows the ratio of the expression level of IL-33 gene in the ear tissue of IL-33 gene transgenic mice. The IL-33 gene expression level of wild-type mouse is 1. C1, C2: wild-type mouse. # No.: hK14mIL33tg primary transgenic candidate mouse.

RNA was extracted from biopsied ear tissue of twelve IL-33 gene transgenic mice obtained in Example 2. Based on the obtained RNA, quantitative real-time RT-PCR was performed using TaqMan probe Mm00505403_m1 (Life Technologies Corp, Carlsbad, Calif.), and the mice high expressing mouse IL-33 gene (1133) were selected. Four out of twelve IL-33 gene transgenic mice were confirmed to show 11- to 41-fold higher expression of IL-33 gene in the ear tissue as compared to wild-type mice (FIG. 2). Using #89 mouse out of them as a founder, mouse lineage hK14mIL33tg #1 (HCM-0374) capable of stably developing dermatitis as mice grow, and transmitting a transgene to germline (hereinafter hK14mIL33tg) could be established. The examination hereafter was performed using an offspring mice obtained by crossing hK14mIL33tg with C57BL/6J mice.

Example 4

Analysis of IL-33 Expression in the Skin of hK14mIL33tg Mice

Figure 3:
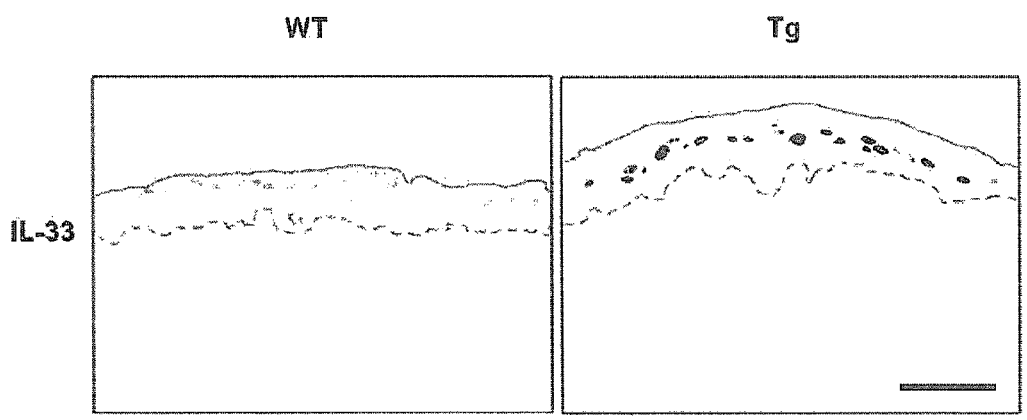
FIG. 3 shows analysis of the IL-33 expression in the ear skin of wild-type mice (WT) and hK14mIL33tg mice (Tg). scale: 50 μm.

Auricle of mice was fixed with 4% para-formaldehyde, embedded in paraffin, and a 4 μm slice was prepared. The slice was reacted with anti-IL-33 polyclonal antibody, and fluorescent stained with Alexa594. The representative results in three experiments are shown in Figure (FIG. 3). Fluorescence intensity is shown in black. The solid line in the Figure shows surface of horny layer and the dotted line shows an epidermis-dermis boundary. As compared to wild-type mice (WT), enhance expression of IL-33 was found in the nucleus of keratinocyte of epidermis of the skin of hK14mIL33tg mice (Tg).

Example 5

Analysis of Tissue Specific Expression of IL-33 Gene in hK14mIL33tg Mice

Figure 4:
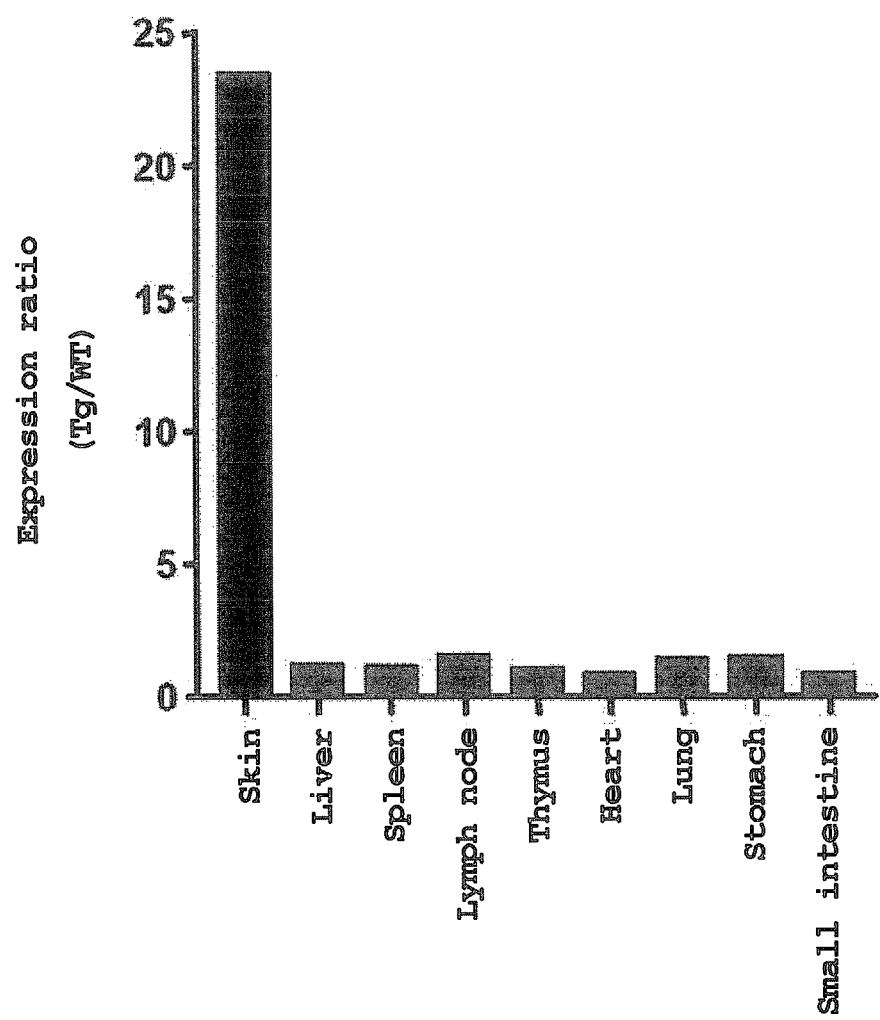
FIG. 4 shows analysis of the tissue specific expression of IL-33 gene in hK14mIL33tg mice. The ratio of IL-33 gene expression level in each organ of hK14mIL33tg mice relative to wild-type mice. A skin-selective increase of IL-33 gene is shown.

Expression of IL-33 gene in each organ of wild-type mice and hK14mIL33tg mice was compared by qPCR. The data of representative results in two experiments are shown (FIG. 4). It was suggested that expression of IL-33 gene was selectively enhanced in the skin as compared to each organ in hK14mIL33tg mice.

Example 6

Macroscopic Observation of Dermatitis in hK14mIL33tg Mice

Figure 5:
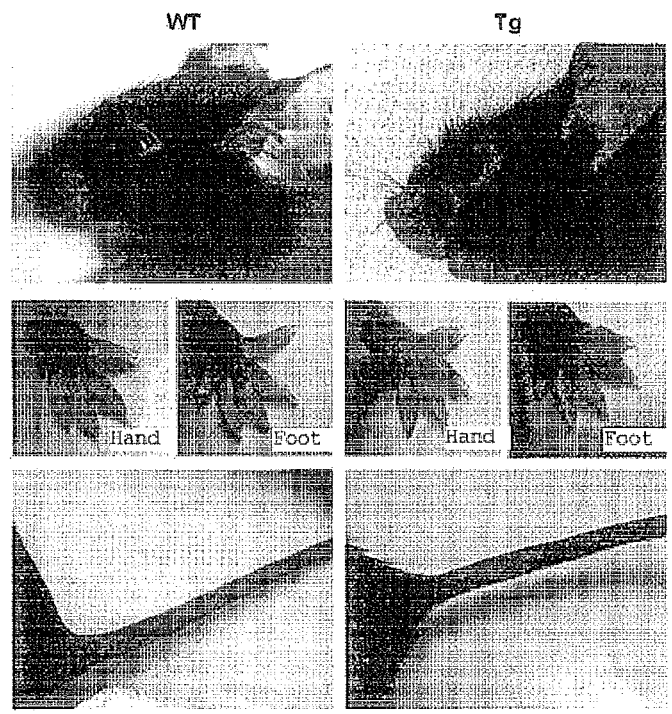
FIG. 5 shows macroscopic pictures of dermatitis in hK14mIL33tg mice (Tg). WT: wild-type mice.

In hK14mIL33tg mice, infiltrative erythema accompanied by crusta, erosion, or desquamation was developed on the face, particularly around eyes, around nose, and neck, auricle, limbs, tail and the like, where hair is less and stimulation from the outside acts easily (FIG. 5). The photographs show representative observations of 24- to 28-week-old mice.

Example 7

Figure 6:
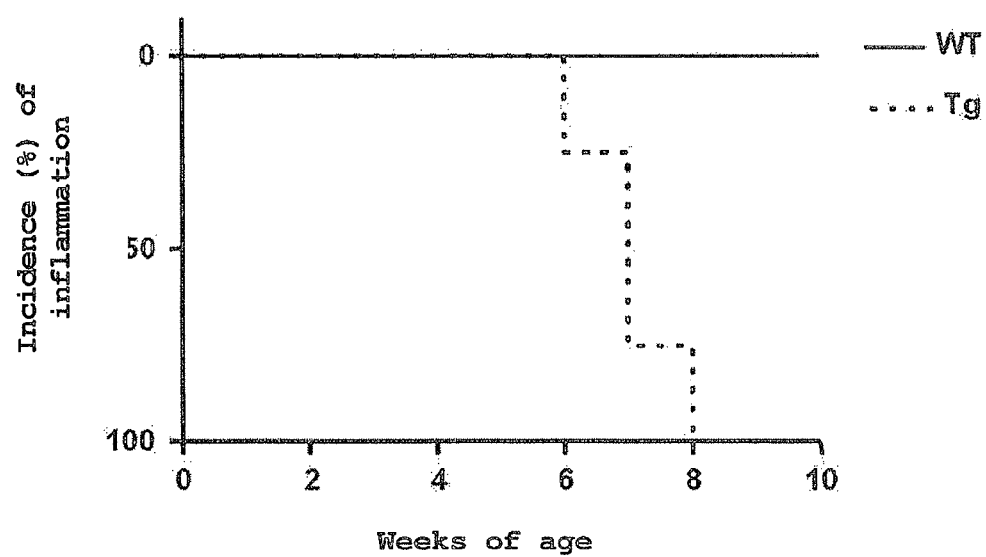
FIG. 6 shows the onset, course and incidence of skin lesion in wild-type mice (WT) and hK14mIL33tg mice (Tg). Detection of significant difference was conducted by a log rank test (two-sided) which was P<0.001 indicating a significant difference.

Onset Progress and Frequency of Skin Lesion in hK14mIL33tg Mice hK14mIL33tg mice was normally born, and normally grown until 6-week-old. As compared to wild-type mice (WT) (n=7), skin lesion was developed from 6-week-old to 8-week-old in hK14mIL33tg mice (Tg) (n=4). After 8-week-old, all hK14mIL33tg mice shows skin lesion (FIG. 6).

Example 8

Observation of Hematoxylin-Eosin Stained Skin Lesion Tissue in hK14mIL33tg Mice

Figure 7:
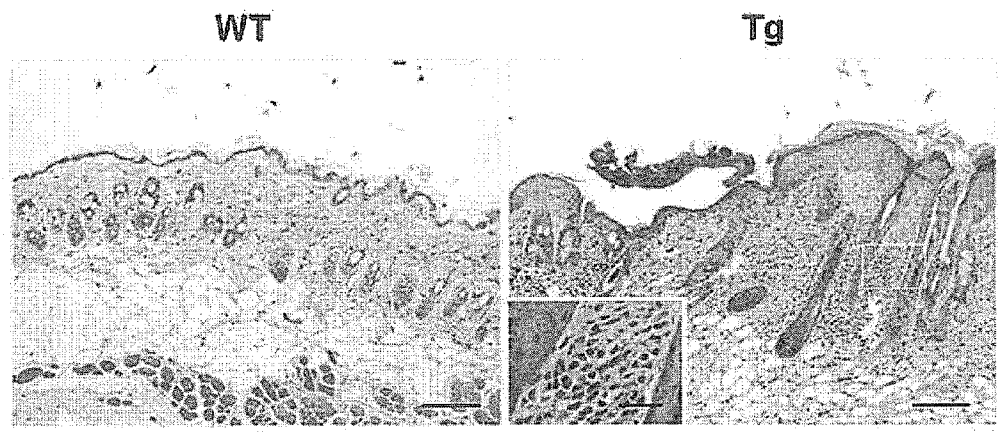
FIG. 7 shows hematoxylin-eosin stained images of skin tissue of wild-type mice (WT) and skin lesion tissue of hK14mIL33tg mice (Tg) (both around the eye). scale; 200 μm; 50 μm (inset).

A skin tissue (around eye) of wild-type mice (WT) and skin lesion tissue (around eye) of hK14mIL33tg mice (Tg) were stained with hematoxylin-eosin. Representative tissue images of two experiments using 3 mice are shown (FIG. 7). In hK14mIL33tg mice, epidermis thickening and inflammatory cell infiltration containing eosinophils in dermis were found.

Example 9

Figure 8:
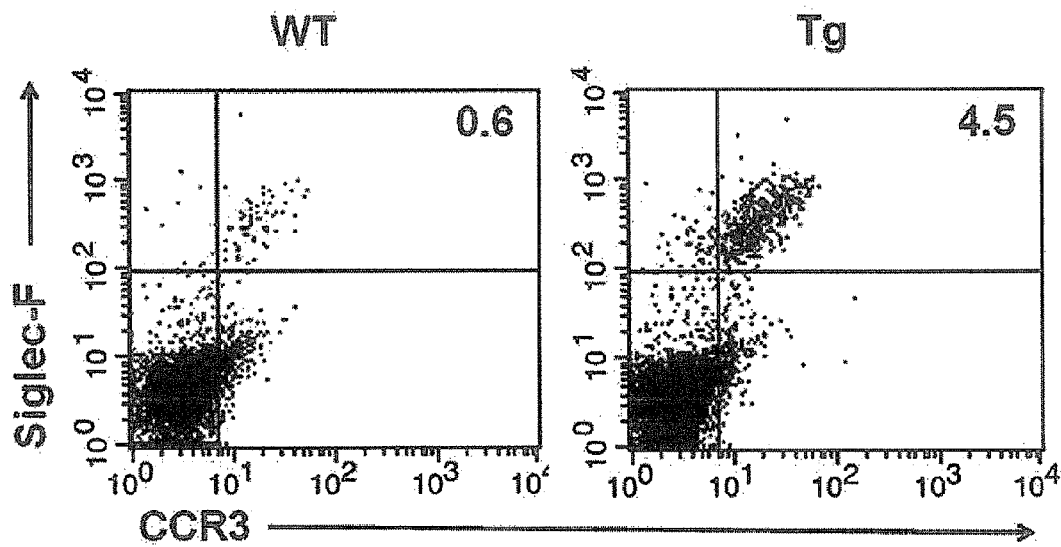
FIG. 8 shows flow cytometry analysis of the skin cells around the eyes of wild-type mice (WT) and hK14mIL33tg mice (Tg). The numerical values show the ratio of CCR3$^+$ Siglec-F$^+$ cells (eosinophils).
Figure 9:
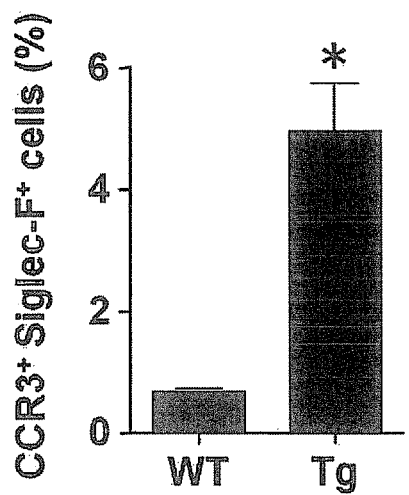
FIG. 9 shows the proportion of CCR3$^+$Siglec-F$^+$ cells (eosinophils) in the skin cells around the eyes of wild-type mice (WT) and hK14mIL33tg mice (Tg). The data shows average±standard error (n=4) *P<0.05 (detected by Student's t-test).

Flow Cytometry Analysis of Skin and Peripheral Blood Eosinophils of hK14mIL33tg Mice Flow cytometry analysis of eosinophil that infiltrates into the skin of wild-type mice (WT) and hK14mIL33tg mice (Tg) was performed. Representative data of two experiments using 4 mice are shown (FIG. 8). The ratio of eosinophil was calculated from the number of skin cells B220$^-$CD3$^-$CD45$^+$, i.e., leukocytes excluding T cells, B cells (corresponding to neutrophils, eosinophils, basophils, mast cells, type 2 innate lymphoid cells and the like). In the skin, a remarkable increase in eosinophil infiltration of CCR3$^+$ Siglec-F$^+$ was found, showing average 7.4-fold in hK14mIL33tg mice as compared to wild-type mice (FIG. 9).

Figure 10:
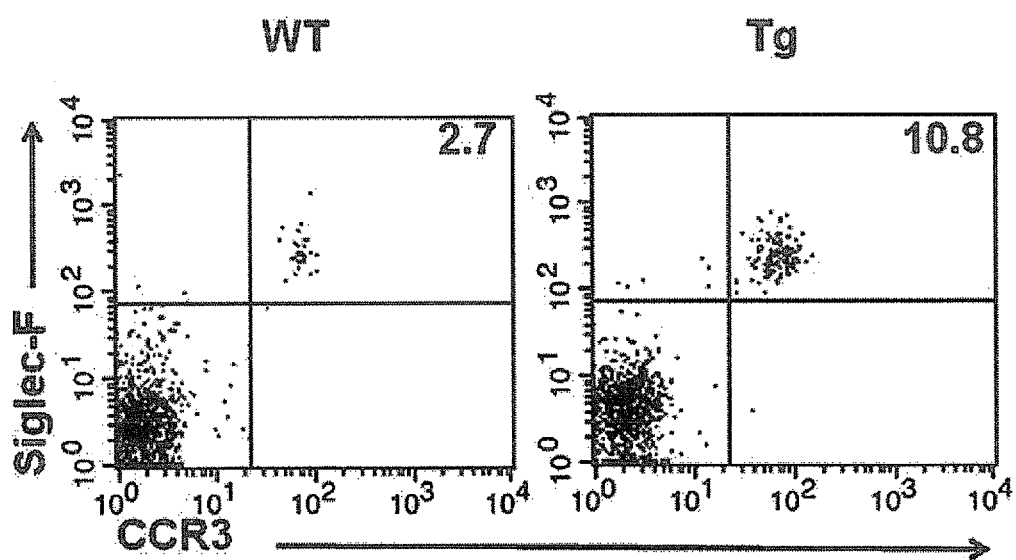
FIG. 10 shows flow cytometry analysis of peripheral blood cells of wild-type mice (WT) and hK14mIL33tg mice (Tg). The numerical values show the ratio of CCR3$^+$Siglec-F$^+$ cells (eosinophils).
Figure 11:
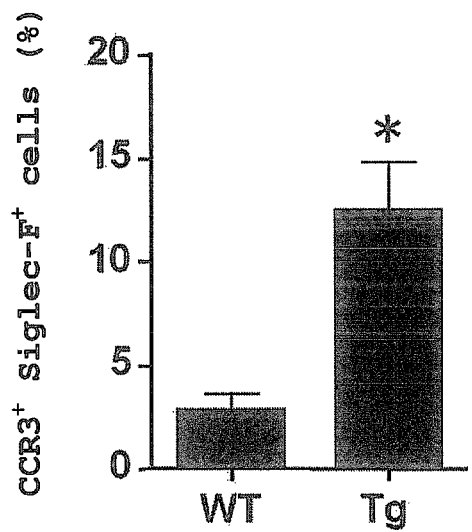
FIG. 11 shows the proportion of CCR3$^+$Siglec-F$^+$ cells (eosinophils) in the peripheral blood cells of wild-type mice (WT) and hK14mIL33tg mice (Tg). The data shows average±standard error (n=4) *P<0.05 (detected by Student's t-test).

Similarly, flow cytometry analysis of peripheral blood cells of wild-type mice (WT) and hK14mIL33tg mice (Tg) was performed. Representative data of two experiments using 4 mice are shown (FIGS. 10, 11). Also in peripheral blood, a significant increase in eosinophil was similarly found in hK14mIL33tg mice, showing average 4.5-fold as compared to wild-type mice.

Figure 12:
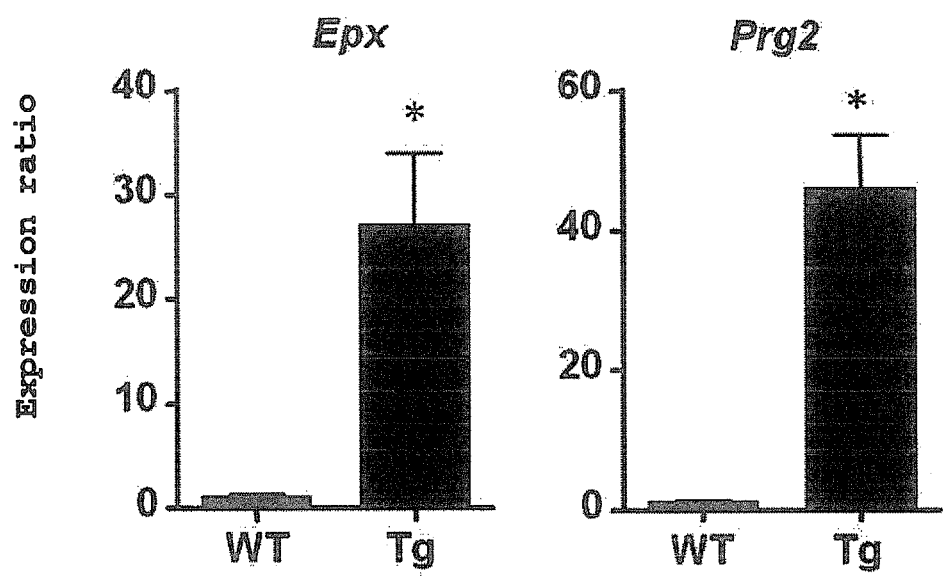
FIG. 12 shows analysis of the expression of the eosinophils peroxidase gene (Epx) and the eosinophils granule major basic protein gene (Erg2) in the skin around the eyes of wild-type mice (WT) and hK14mIL33tg mice (Tg) by quantitative real-time RT-PCR. average±standard error (n=5) *P<0.05 (detected by Student's t-test).

Furthermore, total RNA was prepared from the skin around the eyes, and expression of eosinophil peroxidase (Epx) and eosinophil granule major basic protein gene (Prg2) as eosinophil markers was analyzed by quantitative real-time RT-PCR. As a result, expression of Epx and Prg2 genes was significantly higher in hK14mIL33tg mice (Tg) than in wild-type mice (WT), showing average 26.9-fold, 45.7-fold, respectively (FIG. 12).

Example 10

Figure 13:
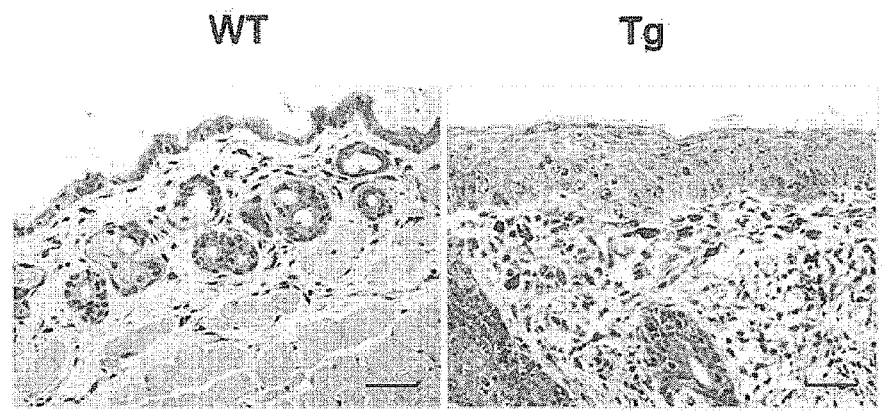
FIG. 13 shows toluidine blue-stained images of skin tissue of wild-type mice (WT) and skin lesion tissue of hK14mIL33tg mice (Tg) (both around the eye). scale; 50 μm.

Observation of Toluidine Blue Staining of Skin Lesion Tissue of hK14mIL33tg Mice A skin tissue (around eye) of wild-type mice (WT) and skin lesion tissue (around eye) of hK14mIL33tg mice (Tg) were stained with toluidine blue. Representative tissue images of two experiments using 3 mice are shown (FIG. 13). As a result of toluidine blue staining, it was found that mast cells of dermis increased in dermatitis lesion tissue produced in hK14mIL33tg mice.

Example 11

Flow Cytometry Analysis of Mast Cells in hK14mIL33tg Mice

Figure 14:
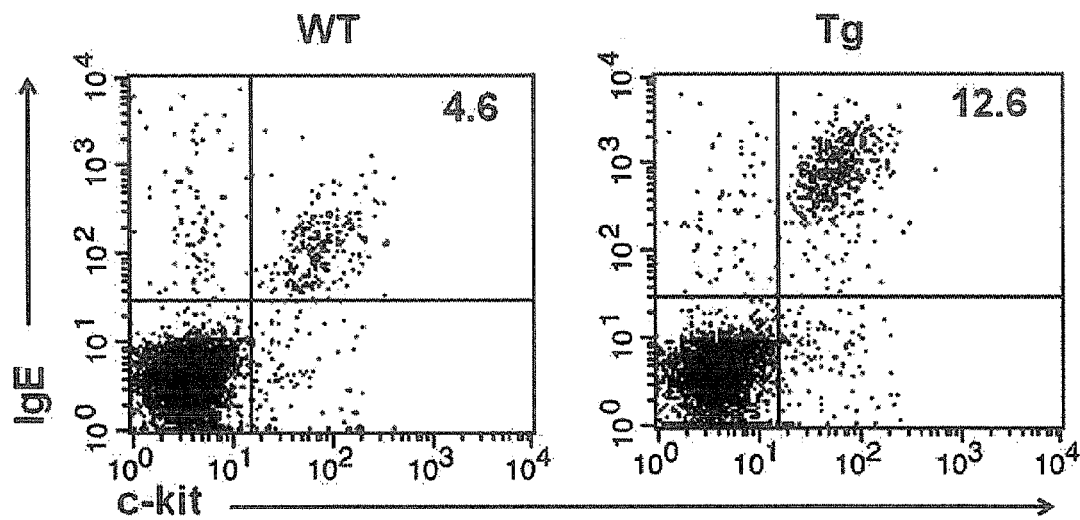
FIG. 14 shows flow cytometry analysis of the skin cells around the eyes of wild-type mice (WT) and hK14mIL33tg mice (Tg). The numerical values show the ratio of c-kit$^+$IgE$^+$ cells (mast cells).
Figure 15:
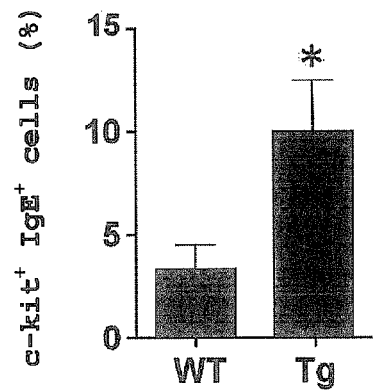
FIG. 15 shows proportion of c-kit$^+$IgE$^+$ cells (mast cells) in the skin cells around the eyes of wild-type mice (WT) and hK14mIL33tg mice (Tg). The data shows average±standard error (n=4) *P<0.05 (detected by Student's t-test).

Flow cytometry analysis of mast cells present in the skin of wild-type mice (WT) or hK14mIL33tg mice (Tg) was performed (FIG. 14). The ratio of mast cells was calculated from flow cytometry analysis of B220$^-$CD3$^-$ cells in the skin (FIG. 15). It was clarified that mast cells, which is c-kit$^+$ IgE$^+$, significantly increased in the skin of lesion of hK14mIL33tg mice, as compared to the normal skin of wild-type mice.

Example 12

Figure 16:
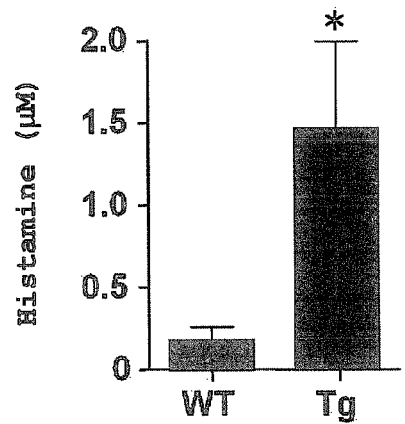
FIG. 16 shows histamine concentration in the plasma of wild-type mice (WT) and hK14mIL33tg mice (Tg). The data shows average±standard error (n=4) *P<0.05 (detected by Student's t-test).
Figure 17:
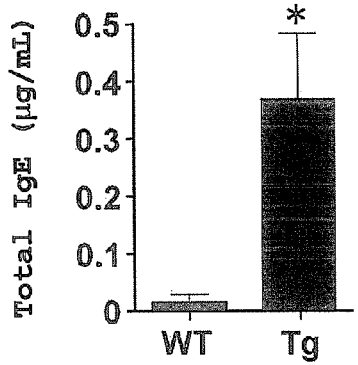
FIG. 17 shows concentration of total IgE in the sera of wild-type mice (WT) and hK14mIL33tg mice (Tg). The data shows average±standard error (n=4) *P<0.05 (detected by Student's t-test).

Analysis of Blood Histamine Concentration and IgE Concentration in hK14mIL33tg Mice Blood plasma was collected from wild-type mice (WT) and hK14mIL33tg mice (Tg), and histamine concentration was measured by ELISA. In addition, serum was collected from wild-type mice and hK14mIL33tg mice, and total IgE concentration was measured by ELISA. The histamine concentration in plasma was average 0.18 µM in wild-type mice, but remarkably high value of average 1.46 µM in hK14mIL33tg mice, and activation of mast cells was suggested in hK14mIL33tg mice (FIG. 16). The total IgE value in the serum was average 15 ng/mL in wild-type mice, whereas the average was 386 ng/mL in hK14mIL33tg mice, showing a high value of not less than 20-fold (FIG. 17).

Example 13

Analysis of Scratching Behavior in hK14mIL33tg Mice

Figure 18:
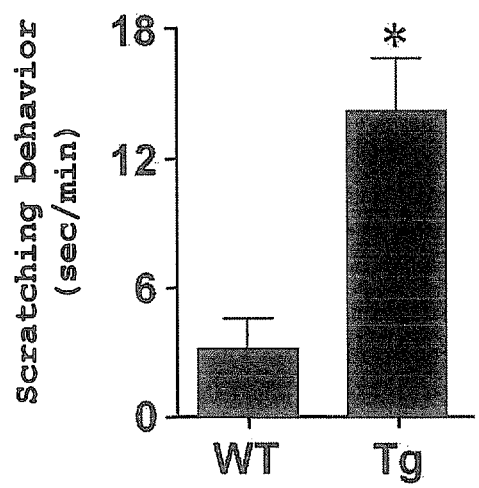
FIG. 18 shows skin scratching time (sec/min) for any 20 min of wild-type mice (WT) and hK14mIL33tg mice (Tg). The data shows average±standard error (n=3) *P<0.05 (detected by Student's t-test).
Figure 19:
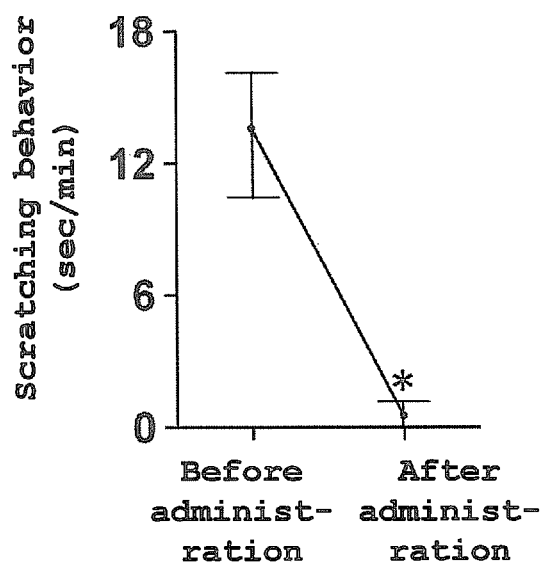
FIG. 19 shows skin scratching time (sec/min) for any 20 min of hK14mIL33tg mice before and after diphenhydramine hydrochloride administration. The data shows average±standard error (n=3) *P<0.05 (detected by Student's t-test).

Skin scratching time (sec/min) in any 20 min of wild-type mice (WT) and hK14mIL33tg mice (Tg) was measured. As compared to wild-type mice, hK14mIL33tg mice showed a significant increase in the scratching time, suggesting strong skin pruritus (itchiness) (FIG. 18). Furthermore, an effect of anti-histamine drugs on the scratching behavior was verified. Diphenhydramine hydrochloride (2 mg) was intraperitoneally administered to hK14mIL33tg mice. As a result, the scratching time of mice observed in 20 min from 6 min after the administration decreased from average 4.6 min to average 0.2 min (FIG. 19). The possibility of mast cells being involved in pruritus due to dermatitis in hK14mIL33tg mice is suggested.

Example 14

Analysis of Cytokine and Chemokine Concentration in hK14mIL33tg Mice

Figure 20:
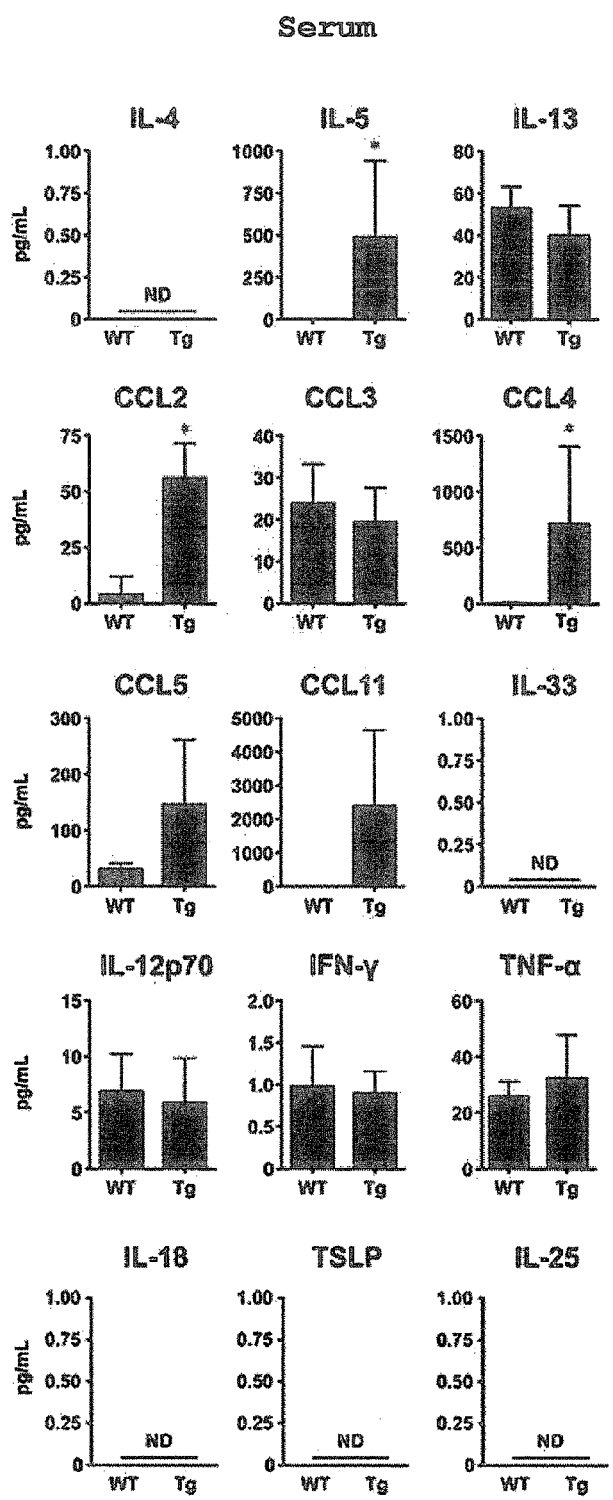
FIG. 20 shows concentration of chemokine and cytokine in the sera of wild-type mice (WT) and hK14mIL33tg mice (Tg). The data shows average±standard error (n=6) *P<0.05 (detected by Student's t-test).
Figure 21:
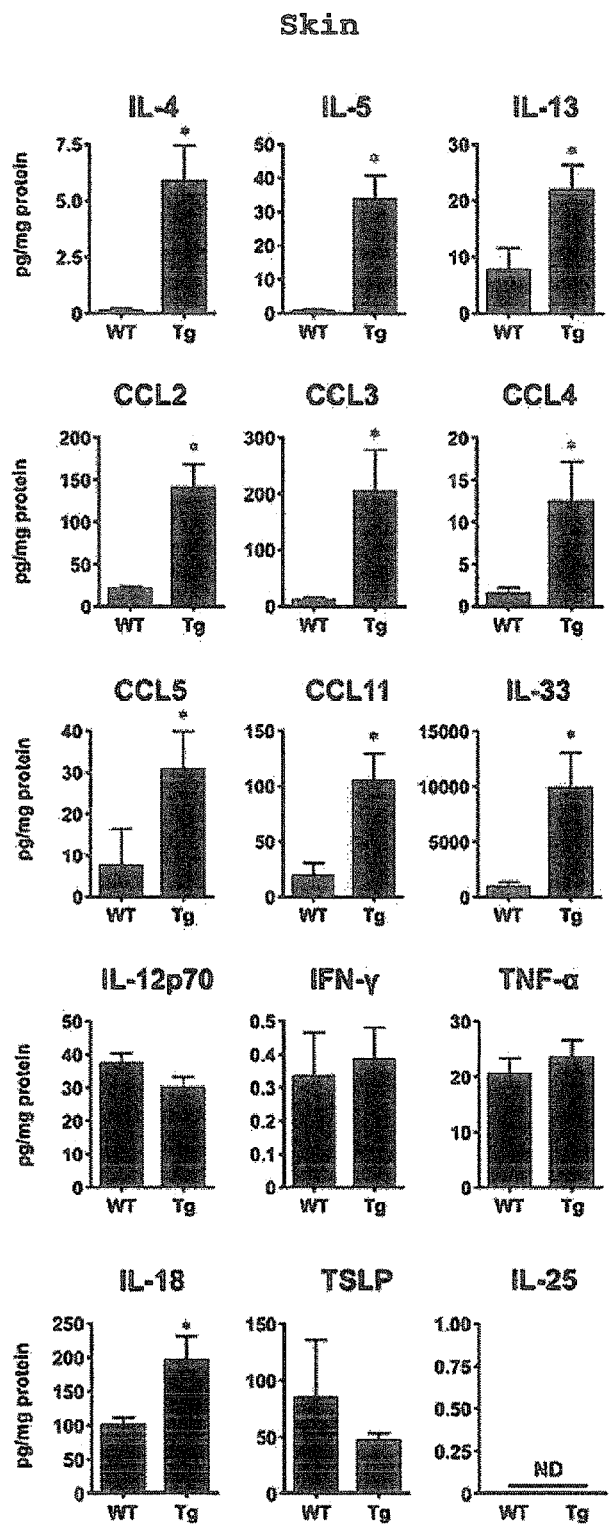
FIG. 21 shows concentration of chemokine and cytokine in the skin extracts of wild-type mice (WT) and hK14mIL33tg mice (Tg). The data shows average±standard error (n=6) *P<0.05 (detected by Student's t-test).

It is known that induction of eosinophils is regulated by Th2 cytokines such as IL-5, IL-13 and the like, chemokines such as RANTES/CCL5, Eotaxin-1/CCL11 and the like, which are ligands that bind to receptor CCR3 expressed by eosinophil. Thus, the concentration of cytokine and chemokine in the sera and extracts of skin around eyes of wild-type mice (WT) and hK14mIL33tg mice (Tg) was comprehensively measured. As compared to wild-type mice, IL-5 showed high values in both the serum and skin of hK14mIL33tg mice (FIGS. 20, 21). In hK14mIL33tg mice, CCL2 and CCL4 increased in both the serum and the skin, and CCL5 and CCL11 increased in the skin (FIGS. 20, 21). These results suggest possibility that these cytokines may play an important role eosinophilic inflammation in hK14mIL33tg mice. On the other hand, Th1 cytokines such as TNF-α, IFN-γ and the like, and IL-12p40 did not change in hK14mIL33tg mice. As for IL-18, TSLP and IL-25 which are epithelial cell-derived cytokines that cause other allergic inflammations, IL-18 increased slightly in skin lesion, and an increase of IL-18 in the serum, which is observed in other dermatitis model mice, was not seen. In addition, a significant increase in TSLP and IL-25 was not seen.

Example 15

Figure 22:
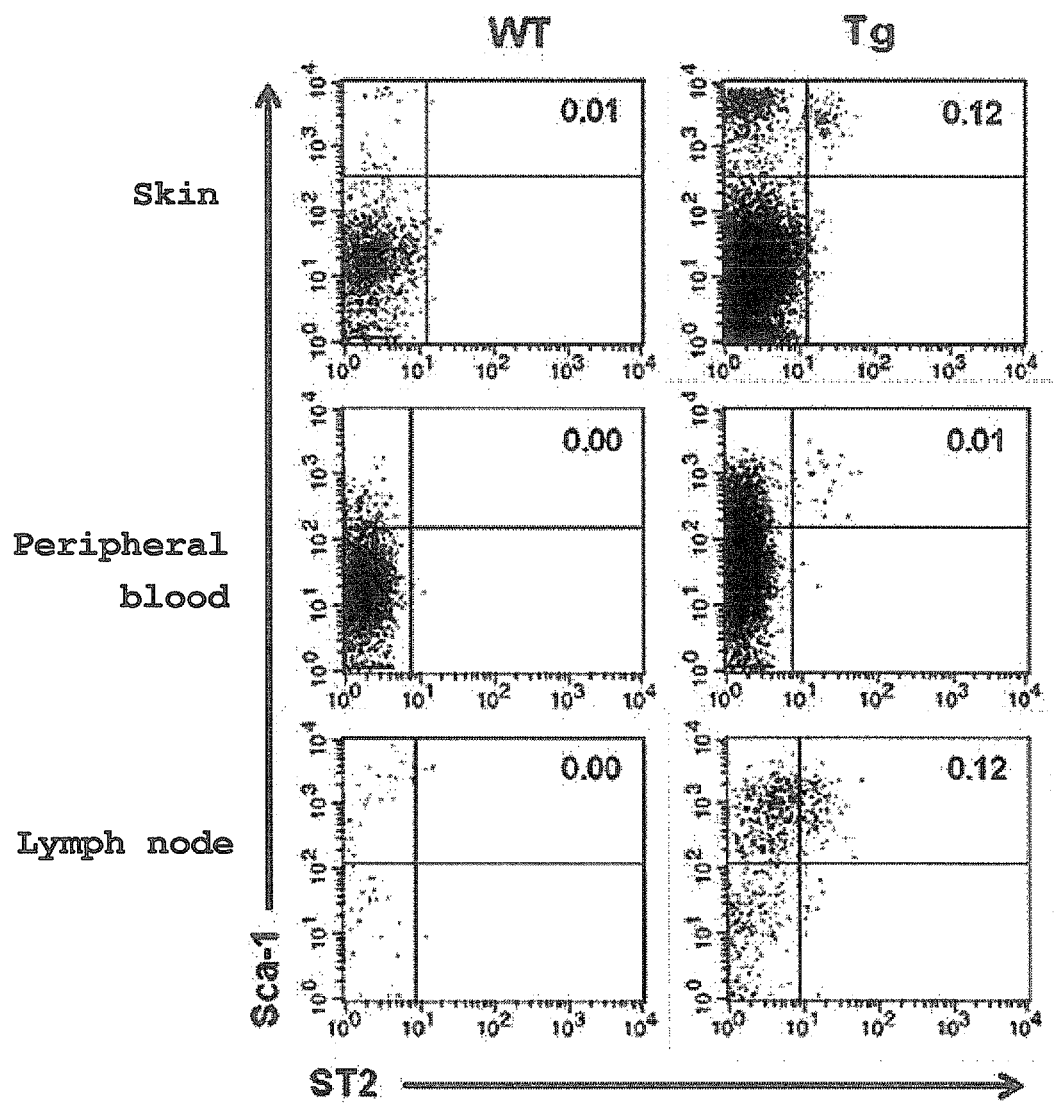
FIG. 22 shows flow cytometry analysis of the skin, peripheral blood and lymph node cells of wild-type mice (WT) and hK14mIL33tg mice (Tg). The numerical values show the proportion of Lin$^-$ ST2$^+$Sca-1$^+$ cells (type 2 innate lymphoid cells) as calculated from the flow cytometry analysis of FSC low value SSC low value cells (lymphocyte gated).
Figure 23:
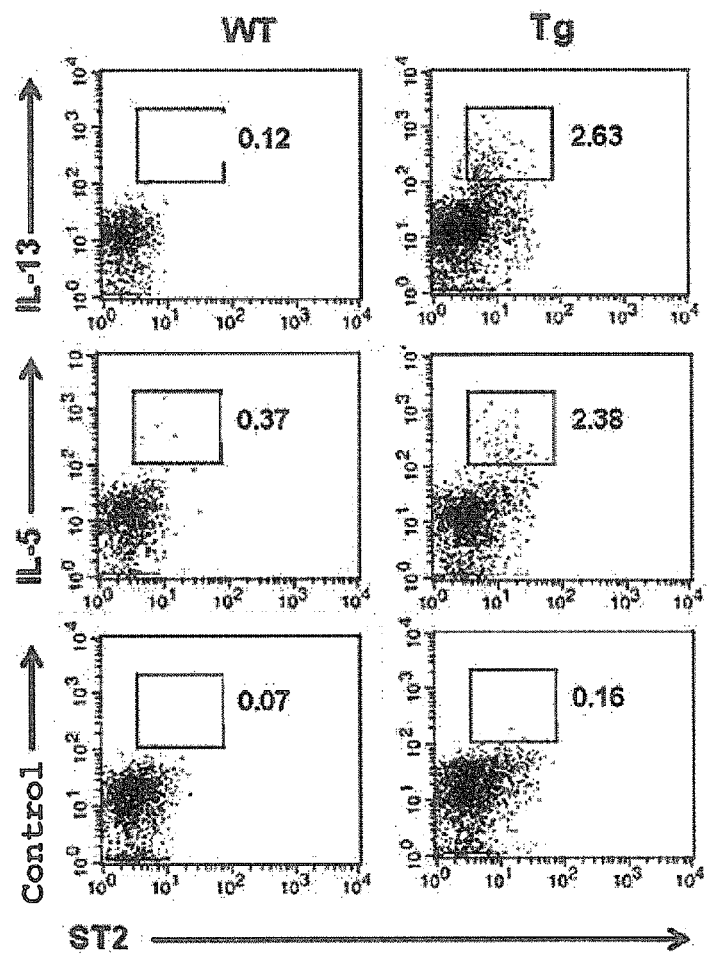
FIG. 23 shows flow cytometry analysis of lymph node cells of wild-type mice (WT) and hK14mIL33tg mice (Tg). The numerical values show the proportion of ST2$^+$IL-5$^+$ or ST2$^+$IL-13$^+$ cells calculated by flow cytometry analysis.
Figure 24:
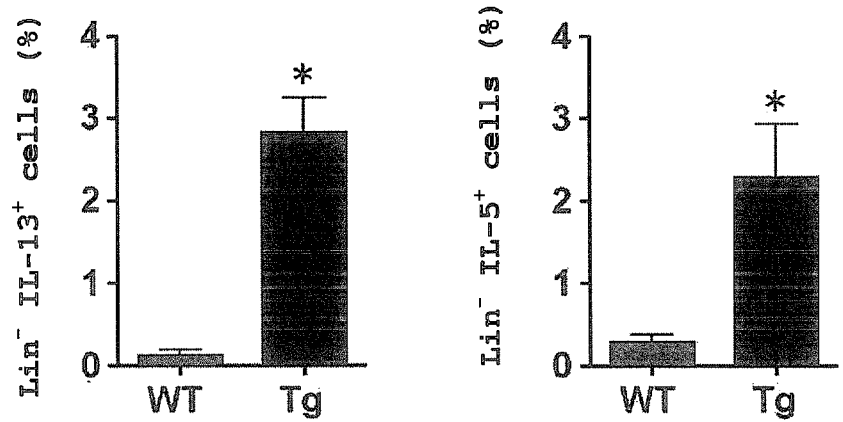
FIG. 24 shows proportion of type 2 innate lymphoid cells that produce IL-5 or IL-13 in lymph node cells of wild-type mice (WT) and hK14mIL33tg mice (Tg). The data shows average±standard error (n=3) *P<0.05 (detected by Student's t-test).

Flow Cytometry Analysis of Skin Infiltrating Cells, Peripheral Blood Cells or Lymph Node Cells in hK14mIL33tg Mice In experiments of lung parasite infection inducing IL-33 (Yasuda K et al., Proc Natl Acad Sci USA, 109:3451-62012, 2012), type 2 innate lymphoid cells are assumed as cells that produces IL-5 in an IL-33-dependent manner. Since enhanced production of IL-5 and IL-13 was seen in hK14mIL33tg mice in Example 14, flow cytometry analysis of cells derived from skin, peripheral blood, and lymph nodes was performed to study whether type 2 innate lymphoid cells that produce these cytokines increased. The cells were gated on lineage marker negative cells fraction. Representative data of two experiments using 3 mice are shown (FIG. 22). As compared to wild-type mice (WT), it was clarified that Lin$^-$ST2$^+$Sca-1$^+$ type 2 innate lymphoid cells increased in topical skin, peripheral blood and lymph nodes in hK14mIL33tg mice (Tg). That is, IL-33 is suggested to be involved in the induction of type 2 innate lymphoid cells. Then, the expression of IL-5, IL-13 in Lin$^-$ ST2$^+$ cells of lymph nodes was analyzed. To identify cells that produces IL-5 and IL-13, intracellular staining was performed. The cells were gated on lineage marker negative cells fraction. Representative data of experiments using 3 mice are shown (FIG. 23). Furthermore, the ratio of Lin⁻ST2⁺IL-5⁺ or Lin⁻ST2⁺IL-13⁺ cells was calculated from the flow cytometry analysis of Lin⁻ cells (FIG. 24). As compared to wild-type mice (WT), type 2 innate lymphoid cells that produce IL-5 or IL-13 increased in the lymph nodes of hK14mIL33tg mice (Tg).

Example 16

Figure 25:
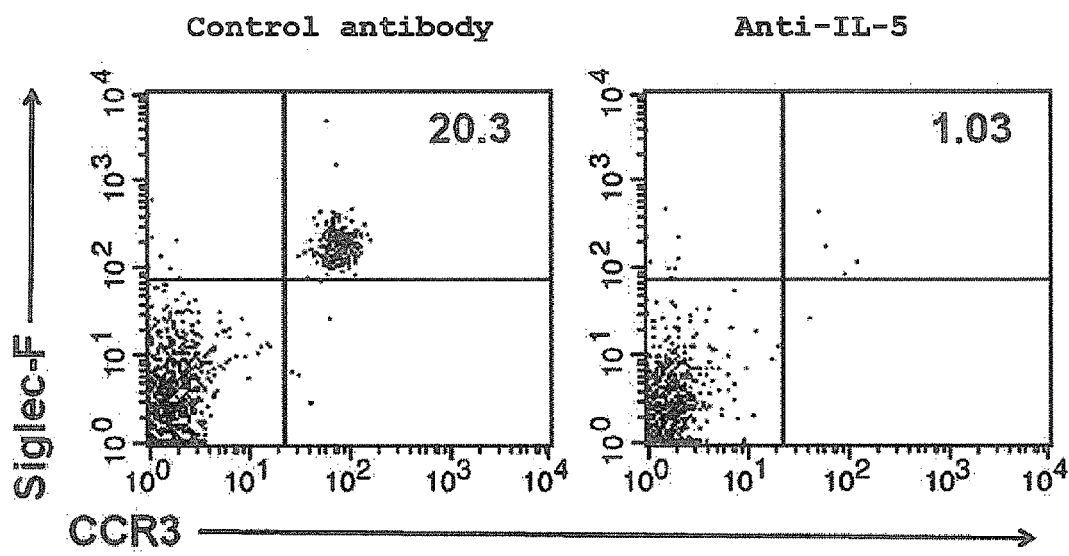
FIG. 25 shows flow cytometry analysis of peripheral blood cells of hK14mIL33tg mice after administration of IL-5 neutralizing antibody or control IgG antibody. The numerical values show the ratio of CCR3$^+$Siglec-F$^+$ cell (eosinophils).
Figure 26:
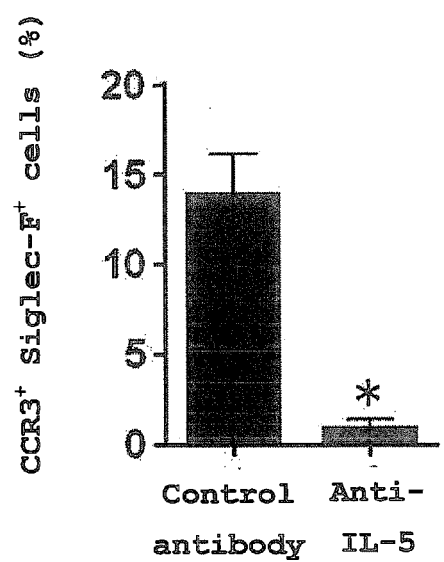
FIG. 26 shows the proportion of CCR3$^+$Siglec-F$^+$ cells (eosinophils) in the peripheral blood cells of hK14mIL33tg mice (Tg) after administration of IL-5 neutralizing antibody or control IgG antibody. The data shows average±standard error (n=4) *P<0.05 (detected by Student's t-test).
Figure 27:
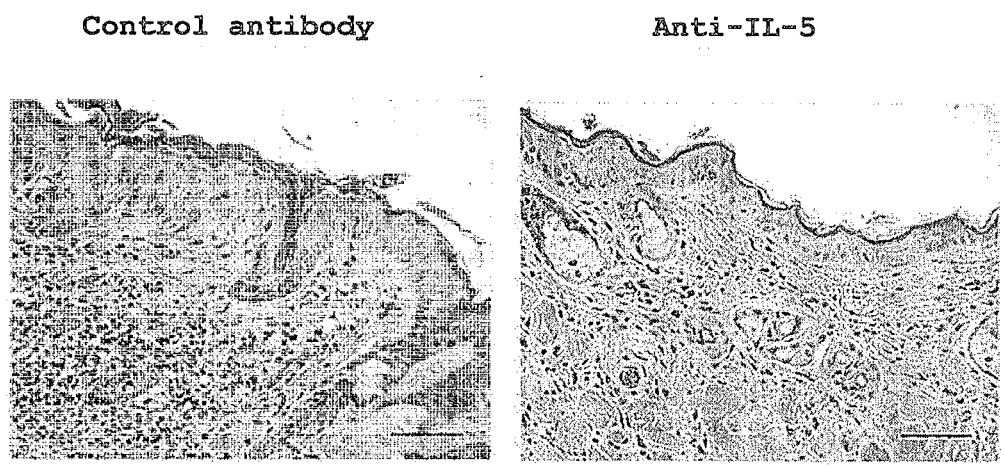
FIG. 27 shows hematoxylin-eosin stained images of skin tissue around the eye of hK14mIL33tg mice after administration of IL-5 neutralizing antibody or control IgG antibody. scale; 50 μm.
Figure 28:
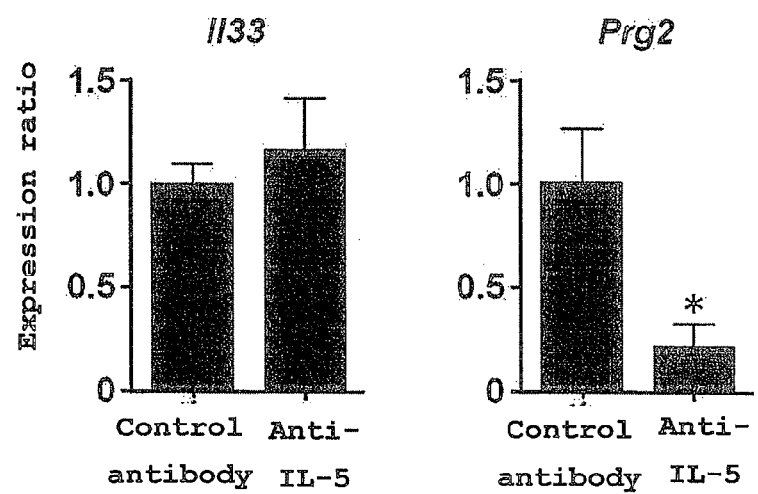
FIG. 28 shows variation of the expression of the IL33 gene and the Prg2 gene in the skin of hK14mIL33tg mice after administration of IL-5 neutralizing antibody or control IgG antibody. The data shows average±standard error (n=4) *P<0.05 (detected by Student's t-test).

Analysis of Effect of Administration of IL-5 Neutralizing Antibody on hK14mIL33tg Mice To clarify whether IL-5 is necessary for increasing eosinophils in hK14mIL33tg mice, control IgG1 antibody (20 μg/mouse) or IL-5 neutralizing antibody (20 μg/mouse) was intraperitoneally administered to hK14mIL33tg mice every 2 days for 2 weeks. Thereafter, flow cytometry analysis of peripheral blood cells of hK14mIL33tg mice was performed. The cells were gated on B220⁻CD3⁻CD45⁺ fraction. Representative data of experiments using 4 mice are shown (FIG. 25). The ratio of the obtained eosinophils was calculated from the flow cytometry analysis of the peripheral blood cell of B220⁻CD3⁻CD45⁺ cells (FIG. 26). In hK14mIL33tg mice in the IL-5 neutralizing antibody administration group, an increase in eosinophils in the peripheral blood was significantly improved as compared to the control group. Furthermore, skin tissue around the eyes of hK14mIL33tg mice was stained with hematoxylin-eosin. Representative Figures of experiments using 4 mice are shown (FIG. 27). In dermatitis lesion, improvement of epidermis thickening and decrease in infiltrating cells were found, and infiltration of eosinophils was also clearly improved. In addition, the expression of the IL-33 and eosinophil granule major basic protein genes (Prg2) in skin lesion tissue was analyzed (FIG. 28). In hK14mIL33tg mice, no change was found in the induction of IL-33 gene expression in the skin, but the expression of Prg2 as an eosinophil marker was significantly decreased by the administration of IL-5 neutralizing antibody. Therefore, the administration of IL-5 neutralizing antibody suppressed eosinophil infiltration into the skin of hK14mIL33tg mice. From the above, it was suggested that IL-5 produced by type 2 innate lymphoid cells and the like is important for increasing eosinophils in hK14mIL33tg mice.

Example 17

Suppression of Scratching Behavior by Steroid Drug in hK14mIL33tg Mice

Figure 29:
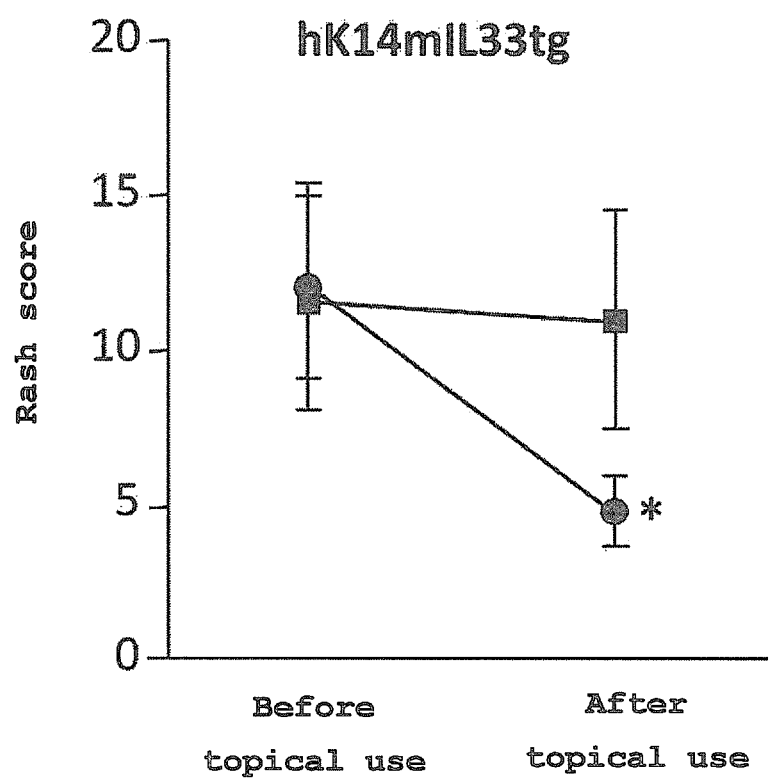
FIG. 29 shows rash score of hK14mIL33tg mice before and after application of white petrolatum or betamethasone butyrate propionate. ■: white petrolatum. ●: betamethasone butyrate propionate. The data shows average±standard error (n=4) *P<0.05 (detected by Student's t-test).

An effect of steroid drug on scratching behavior of hK14mIL33tg mice was verified. White petrolatum as a control, and betamethasone butyrate propionate as a steroid drug were applied to a rash site of hK14mIL33tg mice 5 times every 2 days. As rash scores, 5 items of pruritus, erythematous plaque/bleeding, edema, epidermis detach/erosion, and desquamation/drying were evaluated into absent (0 point), mild (1 point), moderate (2 points), and severe (3 points) (Matsuda H et al., Int. Immunol, 9(3):461-466, 1997). As a result, the total points of rash score decreased from average 12.3 points 15 to 4.8 points after application, and significant improvement could be confirmed (FIG. 29).

INDUSTRIAL APPLICABILITY

The Tg animal of the present invention is useful for the analysis of onset mechanism and pathology of atopic dermatitis, and determination of the effect of therapeutic agents for atopic dermatitis. In addition, IL-33 was clarified to be an extremely important cytokine for the onset of atopic dermatitis. In the future, application to the elucidation of the mechanism of production and extracellular liberation and activation of IL-33, and a regulatory molecule that regulates them and the like is also expected. Furthermore, it is expected to be useful for the development of a novel therapeutic agent for atopic dermatitis which targets IL-33, and a therapeutic drug for asthma, allergic rhinitis and pollinosis in which IL-33 is involved in the pathology, as well as other diseases such as rheumatoid arthritis, inflammatory bowel disease and the like.

This application is based on patent application No. 2013-096637 filed in Japan (filing date: May 1, 2013), the contents of which are incorporated in full herein.

The invention claimed is:

1. A method of screening for a therapeutic compound for atopic dermatitis, comprising,
   (a) providing a transgenic atopic dermatitis mouse whose genome comprises a nucleic acid molecule encoding a functional IL-33 protein under the control of a skin promoter, wherein the mouse exhibits (1) spontaneous onset of dermatitis, (2) increase in number of eosinophils, mast cells, and type 2 innate lymphoid cells, (3) increase in total IgE concentration, histamine concentration, interleukin 4 (IL-4) concentration, interleukin 5 (IL-5) concentration, interleukin 13 (IL-13) concentration, chemokine chronic lymphocytic leukemia 2 (CCL2) concentration, chemokine chronic lymphocytic leukemia 4 (CCL4) concentration, chemokine chronic lymphocytic leukemia 5 (CCL5) concentration, and chemokine chronic lymphocyte leukemia 11 (CCL11) concentration, and (4) increase in scratching time, wherein the transgenic mouse exhibits said phenotype under specific pathogen free (SPF) conditions as compared to a wild type mouse under the SPF conditions,
   (b) administering to said transgenic mouse a test compound,
   (c) determining one or more of the features selected from the group consisting of (i) the number of type 2 innate lymphoid cells, (ii) CCL2 concentration, (iii) CCL4 concentration, (iv) CCL5 concentration, and (v) CCL11 concentration in the transgenic mouse of step (b) as compared to the transgenic mouse of step (a) not administered the test compound, wherein the determining is performed in the atopic dermatitis skin or peripheral blood of said transgenic mouse, and
   (d) selecting a test compound that decreases one or more of the determined features (i)-(v) in step (c) of the transgenic mouse administered the test compound as compared to a transgenic mouse not administered the test compound.

2. The method of claim 1, wherein step (c) further comprises determining one or more features selected from the group consisting of (vi) rash score, (vii) number of mast cells or number of eosinophils, (viii) total IgE concentration, histamine concentration, IL-4 concentration, IL-5 concentration, or IL-13 concentration, and (ix) scratching time.

3. The method of claim 1, wherein the skin promoter is a keratin promoter.

4. The method of claim 3, wherein the keratin promoter is a human keratin 14 promoter.

5. The method of claim 1, wherein the functional IL-33 protein comprises the amino acid sequence as set forth in SEQ ID NO: 2.

6. The method of claim 2, wherein the number of eosinophils increases by 7- to 8-fold in the skin and 4- to 5-fold in the peripheral blood as compared to the transgenic mouse not administered the test compound.

* * * * *

UNITED STATES PATENT AND TRADEMARK OFFICE
CERTIFICATE OF CORRECTION

PATENT NO. : 9,949,465 B2
APPLICATION NO. : 14/888398
DATED : April 24, 2018
INVENTOR(S) : Yamanishi et al.

It is certified that error appears in the above-identified patent and that said Letters Patent is hereby corrected as shown below:

In the Claims

Claim 1, Column 31, Line 24, "lymphocyte leukemia 11" should read "lymphocytic leukemia 11"

Signed and Sealed this
Seventeenth Day of July, 2018

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 801
<212> TYPE: DNA
<213> ORGANISM: Mus musculus
<220> FEATURE:
<221> NAME/KEY: CDS
<222> LOCATION: (1) ... (801)

<400> SEQUENCE: 1 atg aga cct aga atg aag tat tcc aac tcc aag att tcc ccg gca aag        48
Met Arg Pro Arg Met Lys Tyr Ser Asn Ser Lys Ile Ser Pro Ala Lys
1               5                   10                  15 ttc agc agc acc gca ggc gaa gcc ctg gtc ccg cct tgc aaa ata aga        96
Phe Ser Ser Thr Ala Gly Glu Ala Leu Val Pro Pro Cys Lys Ile Arg
            20                  25                  30 aga tcc caa cag aag acc aaa gaa ttc tgc cat gtc tac tgc atg aga       144
Arg Ser Gln Gln Lys Thr Lys Glu Phe Cys His Val Tyr Cys Met Arg
        35                  40                  45 ctc cgt tct ggc ctc acc ata aga aag gag act agt tat ttt agg aaa       192
```

```
Leu Arg Ser Gly Leu Thr Ile Arg Lys Glu Thr Ser Tyr Phe Arg Lys
        50                  55                  60 gaa ccc acg aaa aga tat tca cta aaa tcg ggt acc aag cat gaa gag      240
Glu Pro Thr Lys Arg Tyr Ser Leu Lys Ser Gly Thr Lys His Glu Glu
 65                  70                  75                  80 aac ttc tct gcc tat cca cgg gat tct agg aag aga tcc ttg ctt ggc      288
Asn Phe Ser Ala Tyr Pro Arg Asp Ser Arg Lys Arg Ser Leu Leu Gly
                     85                  90                  95 agt atc caa gca ttt gct gcg tct gtt gac aca ttg agc atc caa gga      336
Ser Ile Gln Ala Phe Ala Ala Ser Val Asp Thr Leu Ser Ile Gln Gly
                100                 105                 110 act tca ctt tta aca cag tct cct gcc tcc ctg agt aca tac aat gac      384
Thr Ser Leu Leu Thr Gln Ser Pro Ala Ser Leu Ser Thr Tyr Asn Asp
            115                 120                 125 caa tct gtt agt ttt gtt ttg gag aat gga tgt tat gtg atc aat gtt      432
Gln Ser Val Ser Phe Val Leu Glu Asn Gly Cys Tyr Val Ile Asn Val
        130                 135                 140 gac gac tct gga aaa gac caa gag caa gac cag gtg cta cta cgc tac      480
Asp Asp Ser Gly Lys Asp Gln Glu Gln Asp Gln Val Leu Leu Arg Tyr
145                 150                 155                 160 tat gag tct ccc tgt cct gca agt caa tca ggc gac ggt gtg gat ggg      528
Tyr Glu Ser Pro Cys Pro Ala Ser Gln Ser Gly Asp Gly Val Asp Gly
                    165                 170                 175 aag aag ctg atg gtg aac atg agt ccc atc aaa gac aca gac atc tgg      576
Lys Lys Leu Met Val Asn Met Ser Pro Ile Lys Asp Thr Asp Ile Trp
                180                 185                 190 ctg cat gcc aac gac aag gac tac tcc gtg gag ctt caa agg ggt gac      624
Leu His Ala Asn Asp Lys Asp Tyr Ser Val Glu Leu Gln Arg Gly Asp
            195                 200                 205 gtc tcg cct ccg gaa cag gcc ttc ttc gtc ctt cac aaa aag tcc tcg      672
Val Ser Pro Pro Glu Gln Ala Phe Phe Val Leu His Lys Lys Ser Ser
        210                 215                 220 gac ttt gtt tca ttt gaa tgc aag aat ctt cct ggc act tac ata gga      720
Asp Phe Val Ser Phe Glu Cys Lys Asn Leu Pro Gly Thr Tyr Ile Gly
225                 230                 235                 240 gta aaa gat aac cag ctg gct cta gtg gag gag aaa gat gag agc tgc      768
Val Lys Asp Asn Gln Leu Ala Leu Val Glu Glu Lys Asp Glu Ser Cys
                    245                 250                 255 aac aat att atg ttt aag ctc tcg aaa atc taa                          801
Asn Asn Ile Met Phe Lys Leu Ser Lys Ile
                260                 265

<210> SEQ ID NO 2
<211> LENGTH: 266
<212> TYPE: PRT
<213> ORGANISM: Mus musculus

<400> SEQUENCE: 2

Met Arg Pro Arg Met Lys Tyr Ser Asn Ser Lys Ile Ser Pro Ala Lys
 1               5                  10                  15

Phe Ser Ser Thr Ala Gly Glu Ala Leu Val Pro Pro Cys Lys Ile Arg
                20                  25                  30

Arg Ser Gln Gln Lys Thr Lys Glu Phe Cys His Val Tyr Cys Met Arg
            35                  40                  45

Leu Arg Ser Gly Leu Thr Ile Arg Lys Glu Thr Ser Tyr Phe Arg Lys
        50                  55                  60

Glu Pro Thr Lys Arg Tyr Ser Leu Lys Ser Gly Thr Lys His Glu Glu
 65                  70                  75                  80

Asn Phe Ser Ala Tyr Pro Arg Asp Ser Arg Lys Arg Ser Leu Leu Gly
```

```
            85                  90                  95
Ser Ile Gln Ala Phe Ala Ala Ser Val Asp Thr Leu Ser Ile Gln Gly
        100                 105                 110

Thr Ser Leu Leu Thr Gln Ser Pro Ala Ser Leu Ser Thr Tyr Asn Asp
    115                 120                 125

Gln Ser Val Ser Phe Val Leu Glu Asn Gly Cys Tyr Val Ile Asn Val
130                 135                 140

Asp Asp Ser Gly Lys Asp Gln Glu Gln Asp Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
                180                 185                 190

Leu His Ala Asn Asp Lys Asp Tyr Ser Val Glu Leu Gln Arg Gly Asp
            195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
                260                 265

<210> SEQ ID NO 3
<211> LENGTH: 40
<212> TYPE: DNA
<213> ORGANISM: Artificial Sequence
<220> FEATURE:
<223> OTHER INFORMATION: Synthetic primer

<400> SEQUENCE: 3
gggcgaatac ggatcatgag acctagaatg aagtattcca                     40

<210> SEQ ID NO 4
<211> LENGTH: 40
<212> TYPE: DNA
<213> ORGANISM: Artificial Sequence
<220> FEATURE:
<223> OTHER INFORMATION: Synthetic primer

<400> SEQUENCE: 4
ggactctaga ggatcttaga ttttcgagag cttaaacata                     40

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5 ggaggggggca aagttttcag ggtg                                     24

<210> SEQ ID NO 6
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 6
tttgcaaggc gggaccaggg                                          20
```